US008883271B2

(12) United States Patent
Sakamoto et al.

(10) Patent No.: US 8,883,271 B2
(45) Date of Patent: *Nov. 11, 2014

(54) POLYMERIZABLE CHIRAL COMPOUND, POLYMERIZABLE LIQUID CRYSTAL COMPOUND, LIQUID CRYSTAL POLYMER AND OPTICALLY ANISOTROPIC BODY

(75) Inventors: Kei Sakamoto, Tokyo (JP); Kentaro Tamura, Tokyo (JP); Kumi Okuyama, Tokyo (JP)

(73) Assignee: Zeon Corporation, Tokyo (JP)

( * ) Notice: Subject to any disclaimer, the term of this patent is extended or adjusted under 35 U.S.C. 154(b) by 88 days.

This patent is subject to a terminal disclaimer.

(21) Appl. No.: 13/637,569
(22) PCT Filed: Mar. 10, 2011
(86) PCT No.: PCT/JP2011/055711
§ 371 (c)(1),
(2), (4) Date: Sep. 26, 2012

(87) PCT Pub. No.: WO2011/122298
PCT Pub. Date: Oct. 6, 2011

(65) Prior Publication Data
US 2013/0023637 A1    Jan. 24, 2013

(30) Foreign Application Priority Data

Mar. 31, 2010    (JP) .................................. 2010-084077

(51) Int. Cl.
*C09K 19/52*    (2006.01)
*C09K 19/54*    (2006.01)
(Continued)

(52) U.S. Cl.
CPC ....... *C09K 19/588* (2013.01); *C09K 2019/0448* (2013.01); *C09K 2019/323* (2013.01); *C09K 19/44* (2013.01); *C07D 493/04* (2013.01); *C09K 19/322* (2013.01); *C09K 19/24* (2013.01); *C09K 2019/3408* (2013.01); *C09K 19/12* (2013.01); *C07C 251/88* (2013.01)
USPC ..................... 428/1.1; 252/299.01; 252/299.5; 252/299.61; 252/299.62; 549/464; 560/34; 560/100; 562/439; 562/560

(58) Field of Classification Search
USPC ............ 428/1.1; 252/299.61, 299.62, 299.67; 549/464; 560/34, 100; 562/439, 560
See application file for complete search history.

(56) References Cited

U.S. PATENT DOCUMENTS 5,593,617 A    1/1997 Kelly et al.
5,744,057 A    4/1998 Meyer et al.
(Continued)

FOREIGN PATENT DOCUMENTS

CN    1177592 A    4/1998
EP    0606940 A2    7/1994
(Continued)

OTHER PUBLICATIONS

International Search Report for PCT/JP2011/055711 mailed on Apr. 12, 2011.

*Primary Examiner* — Shean C Wu
(74) *Attorney, Agent, or Firm* — Birch, Stewart, Kolasch & Birch, LLP

(57) ABSTRACT

The present invention is to provide a novel polymerizable chiral compound (chiral agent) having high left-handed helical twisting power, a polymerizable liquid crystal composition comprising the polymerizable chiral compound and a polymerizable liquid crystal compound, a liquid crystal polymer, and an optically anisotropic body.

The object was achieved by a left-handed-helix-inducing polymerizable chiral compound represented by the following formula (I), a polymerizable liquid crystal composition comprising the polymerizable chiral compound and a polymerizable liquid crystal compound, a liquid crystal polymer and an optically anisotropic body:

[Chemical Formula 1]

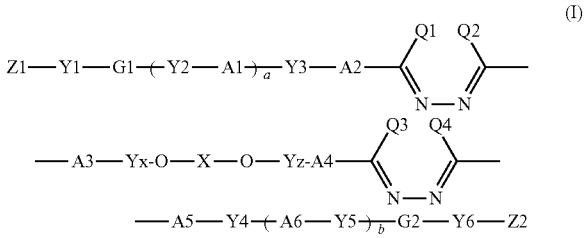

wherein X represents the following formula (X-i) or (X-ii) wherein * represents a bond:

[Chemical Formula 2]

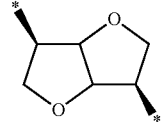

(X-i)

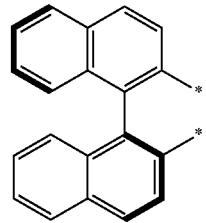

(X-ii)

wherein Y1 to Y6 are each one selected from the group consisting of —O—, —S—, —O—C(=O)—, —C(=O)—O— and so on; Yx is one selected from the group consisting of —C(=O)—, —O—C(=O)—, —CH=CH—C(=O)—, —CH$_2$— and so on; Yz is one selected from the group consisting of —C(=O)—, —C(=O)—O—, —C(=O)—CH=CH— and so on; G1 and G2 are each a divalent aliphatic group which has 1 to 20 carbon atoms and which may have a substituent; Z1 and Z2 are each an alkenyl group which has 2 to 10 carbon atoms and which may be substituted by a halogen atom; Q1 to Q4 are each a hydrogen atom or an alkyl group which has 1 to 6 carbon atoms and which may have a substituent; A1 to A6 are each a divalent organic group having 1 to 30 carbon atoms; and a and b are each 0 or 1.

10 Claims, No Drawings

(51) Int. Cl.

*C09K 19/32* (2006.01)
*C09K 19/34* (2006.01)
*C09K 19/38* (2006.01)
*C07C 243/18* (2006.01)
*C07C 251/88* (2006.01)
*C07D 493/04* (2006.01)
*C09K 19/44* (2006.01)
*C09K 19/58* (2006.01)
*C09K 19/24* (2006.01)
*C09K 19/12* (2006.01)
*C09K 19/04* (2006.01)

(56) References Cited

U.S. PATENT DOCUMENTS

| | | | |
|---|---|---|---|
| 6,010,642 | A | 1/2000 | Takatsu et al. |
| 6,180,028 | B1 | 1/2001 | Hotaka et al. |
| 6,468,444 | B1 | 10/2002 | Meyer et al. |
| 6,723,395 | B2 | 4/2004 | May et al. |
| 8,603,357 | B2 * | 12/2013 | Sakamoto et al. ......... 252/299.6 |
| 2003/0072893 | A1 | 4/2003 | Nakano et al. |
| 2003/0219548 | A1 | 11/2003 | Meyer et al. |
| 2010/0258764 | A1 | 10/2010 | Sakamoto et al. |
| 2011/0140041 | A1* | 6/2011 | Sakamoto et al. ....... 252/299.62 |
| 2011/0186777 | A1* | 8/2011 | Sakamoto et al. ....... 252/299.61 |

FOREIGN PATENT DOCUMENTS

| | | |
|---|---|---|
| EP | 0720041 A2 | 7/1996 |
| EP | 0747382 A1 | 12/1996 |
| GB | 2312529 A | 10/1997 |
| GB | 2330139 A | 4/1999 |
| JP | 62-70406 A | 3/1987 |
| JP | 8-104870 A | 4/1996 |
| JP | 9-20781 A | 1/1997 |
| JP | 9-31077 A | 2/1997 |
| JP | 10-147562 A | 6/1998 |
| JP | 11-71338 A | 3/1999 |
| JP | 11-100575 A | 4/1999 |
| JP | 11-130729 A | 5/1999 |
| JP | 11-193287 A | 7/1999 |
| JP | 2000-309589 A | 11/2000 |
| JP | 2002-265421 A | 9/2002 |
| JP | 2002-308832 A | 10/2002 |
| JP | 2002-533742 A | 10/2002 |
| JP | 2003-137887 A | 5/2003 |
| JP | 2005-263789 A | 9/2005 |
| JP | 2005-309255 A | 11/2005 |
| JP | 2008-170835 A | 7/2008 |
| JP | 2008-291218 A | 12/2008 |
| JP | 2009-167378 A | 7/2009 |
| JP | 2011032179 A * | 2/2011 |
| WO | WO 96/02016 A2 | 1/1996 |
| WO | WO 98/08135 A1 | 2/1998 |
| WO | WO 00/37585 A1 | 6/2000 |
| WO | WO 2008/133290 A1 | 11/2008 |
| WO | WO 2009/078431 A1 | 6/2009 |
| WO | WO 2010038591 A1 * | 4/2010 |

* cited by examiner

POLYMERIZABLE CHIRAL COMPOUND, POLYMERIZABLE LIQUID CRYSTAL COMPOUND, LIQUID CRYSTAL POLYMER AND OPTICALLY ANISOTROPIC BODY

TECHNICAL FIELD

The present invention relates to a novel left-handed-helix-inducing polymerizable chiral compound, a left-handed helical polymerizable liquid crystal composition comprising the polymerizable chiral compound, a left-handed helical liquid crystal polymer obtained by polymerization of the polymerizable liquid crystal composition, and an optically anisotropic body comprising the liquid crystal polymer as a constitutional material.

BACKGROUND ART

A resin layer having cholesteric regularity (hereinafter, it will be referred to as "cholesteric resin layer") has a characteristic of reflecting a circular polarized light which is in a rotational direction that is the same as the direction of helical rotation of cholesteric regularity (hereinafter, the characteristic will be referred to as "selective reflection characteristic"). To produce an optically anisotropic body that serves a purpose, it is needed to separate a circular polarized light which is in a rotational direction depending on the purpose. To do this, it is needed to obtain cholesteric regularities in right- and left-handed helical rotational directions.

If it is possible to form a circularly polarized light separating sheet comprising a cholesteric resin layer having the selective reflection band in the near-infrared light wavelength range, of incident near-infrared light, the circularly polarized light separating sheet can reflect only the circularly polarized light of a specific wavelength. If cholesteric regularities in right- and left-handed helical rotational directions can be obtained, it becomes possible to obtain an infrared reflection thin film with a reflectivity of 100%, for example.

To form the cholesteric resin layer having the selective reflection band in the visible light wavelength range, various chiral agents have been studied.

For example, Patent Literature 1 discloses a chiral compound described by the formula $(Z^{11}\text{---}Y^{11}\text{-}A^{11}\text{-}O\text{---}CO\text{---}O\text{-}M^{11}\text{-}Y^{12})r^1X^a$ wherein $A^{11}$ is a spacer; $M^{11}$ is a mesogenic group; each of $Y^{11}$ and $Y^{12}$ is a chemical bond, —O—, —S—, —CO—O—, —O—CO—, —O—CO—O— or the like; $r^1$ is 2 to 6; $X^a$ is an $r^1$-valent chiral group; and $Z^{11}$ is (a1) at least one of these groups is a reactive group which can participate in a polyaddition reaction, (a2) at least two of these radicals are substituents carrying a reactive group which can participate in a polycondensation reaction, and $Z^{11}$ is a hydrogen or an unreactive radical as long as the condition (a1) or (a2) is satisfied.

Patent Literature 2 discloses a chiral compound described by the formula $(Z^{12}\text{---}Y^{13}\text{-}A^{12}\text{-}Y^{14}\text{-}M^{12}\text{-}Y^{15})r^2X^b$ wherein $A^{12}$ is a spacer; $M^{12}$ is a mesogenic group; each of $Y^{13}$ to $Y^{15}$ is a chemical bond, —O—, —S—, —CO—O—, —O—CO— or the like; $r^2$ is 2 to 6; $X^b$ is an $r^2$-valent chiral group; and $Z^{12}$ is (a3) at least one of these groups is a group with an isocyanate, isothiocyanate, thiirane, aziridine, carboxyl, hydroxyl or amino group, (b2) the other group or each of the other groups is an unreactive group or H.

Patent Literature 3 discloses a compound described by the formula $(Z^{13}\text{---}Y^{16}\text{-}[A^{13}]r^3\text{-}Y^{17}\text{-}M^{13}\text{-}Y^{18}\text{-})r^4X^c$ wherein $A^{13}$ is a spacer; $M^{13}$ is a mesogenic group containing two phenylene radicals which are unsubstituted or substituted via —O—, —CO—, —O—CO—O— or the like; each of $Y^{16}$ to $Y^{18}$ is a single bond, —O—, —S—, —CO—O—, —O—CO— or the like; $Z^{13}$ is a polymerizable group; $r^3$ is 0 or 1; $r^4$ is 2 to 6; and $X^c$ is a chiral group. In Patent Literature 3, a left-handed-helix-inducing compound is also disclosed.

Patent Literature 4 discloses a chiral dopant described by the formula $Z^{14}\text{---}Y^{19}\text{-}(A^{14})r^5\text{-}Y^{20}\text{-}M^{14}\text{-}Y^{21}\text{---}X^d\text{---}Y^{22}\text{-}(A^{15})r^6\text{-}Y^{23}\text{---}Z^{15}$ wherein each of $A^{14}$ and $A^{15}$ is a spacer with a C1 to C30 chain length; each of $Y^{19}$ to $Y^{23}$ is a chemical bond, —O—, —S—, —C(=O)—, —C(=O)—O—, —O—C(=O)—, —CH=CH—C(=O)—O—, —O—C(=O)—O— or the like; $M^{14}$ is a mesogenic group; each of $Z^{14}$ and $Z^{15}$ is a C1 to C4 alkyl, a polymerizable group, a radical having a polymerizable group, or the like; $X^d$ is a dianhydrohexitol group; and each of $r^5$ and $r^6$ is 0 or 1.

Patent Literature 5 discloses that the isosorbide derivative typified by the compound represented by the following formula is useful as a chiral dopant:

[Chemical Formula 1]

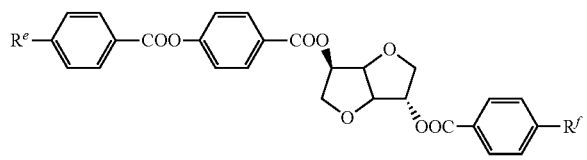

wherein each of $R^e$ and $R^f$ is Ps-Sp-$X^e$, an unsubstituted alkyl group, an alkyl group which may be substituted by —O—, —S—, —NH—, —CO—, —COO—, —OCO— or the like, etc.; Ps is a polymerizable group; Sp is a spacer group or a single bond; and $X^e$ is a single bond, —O—, —S—, —OCH$_2$—, —CH$_2$O—, —CO—, —COO—, —OCO—, —OCO—O—, —OCH$_2$—, —CH$_2$O— or the like.

However, many of the compounds disclosed in these literatures are right-handed-helix-inducing polymerizable chiral compounds and they are not left-handed-helix-inducing polymerizable chiral compounds. A left-handed-helix-inducing polymerizable chiral compound is exemplified only in Patent Literature 1; however, many of the polymerizable chiral compounds disclosed in this literature have no description regarding their helical twisting power (HTP) or have low HTP and thus have a problem of low solubility and compatibility.

CITATION LIST

Patent Literature 1: Japanese Patent Application Laid-Open (JP-A) No. H9-20781 (Corresponding foreign patent applications thereof include U.S. Pat. No. 5,744,057 and EP750029.)
Patent Literature 2: JP-A No. H9-31077 (Corresponding foreign patent applications thereof include EP747382.)
Patent Literature 3: JP-A No. 11-193287 (Corresponding foreign patent applications thereof include GB2330139.)
Patent Literature 4: JP-A No. 2000-309589 (Corresponding foreign patent applications thereof include U.S. Pat. No. 6,468,444 and EP1038941.)
Patent Literature 5: JP-A No. 2003-137887 (Corresponding foreign patent applications thereof include U.S. Pat. No. 6,723,395 and EP1273585.)

SUMMARY OF INVENTION

Technical Problem

The present invention was achieved in view of the above circumstances. An object of the present invention is to provide a novel left-handed-helix-inducing polymerizable chiral compound, a left-handed helical polymerizable liquid crystal composition comprising the polymerizable chiral compound, a left-handed helical liquid crystal polymer obtained by polymerization of the polymerizable liquid crystal composition, and an optically anisotropic body comprising the liquid crystal polymer as a constitutional material.

Solution to Problem

As a result of diligent researches, the inventors of the present invention found out that a polymerizable chiral compound represented by the below-described formula (I) is a left-handed-helix-inducing polymerizable chiral compound with excellent solubility and compatibility. They also found out that a left-handed helical liquid crystal polymer with high helical twisting power (HTP) can be obtained by using the polymerizable chiral compound. Based on these findings, the inventors of the present invention accomplished the present invention.

First, the present invention provides the following left-handed-helix-inducing polymerizable chiral compounds (1) to (7).

(1) A left-handed-helix-inducing polymerizable chiral compound represented by the following formula (I):

[Chemical Formula 2]

$$Z1-Y1-G1-(Y2-A1)_a-Y3-A2-\underset{N-N}{\overset{Q1\ Q2}{\diamond}}-A3-Yx-O-X-O-Yz-A4-\underset{N-N}{\overset{Q3\ Q4}{\diamond}}-A5-Y4-(A6-Y5)_b-G2-Y6-Z2 \quad (I)$$

wherein X represents the following formula (X-i) or (X-ii);

[Chemical Formula 3]

(X-i)

(X-ii)

wherein * represents a bond;
wherein Y1 to Y6 are each independently one selected from the group consisting of a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$— and —NR$^1$—O—, and R$^1$ is a hydrogen atom or an alkyl group having 1 to 6 carbon atoms;

wherein Yx is one selected from the group consisting of a chemical single bond, —C(=O)—, —O—C(=O)—, —NR$^2$—C(=O)—, —CH=CH—C(=O)—, —CH$_2$—, —C$_2$H$_4$— and —CF$_2$—, and R$^2$ is a hydrogen atom or an alkyl group having 1 to 6 carbon atoms;

wherein Yz is one selected from the group consisting of a chemical single bond, —C(=O)—, —C(=O)—O—, —C(=O)—NR$^3$—, —C(=O)—CH=CH—, —CH$_2$—, —C$_2$H$_4$— and —CF$_2$—, and R$^3$ is a hydrogen atom or an alkyl group having 1 to 6 carbon atoms;

wherein G1 and G2 are each independently a divalent aliphatic group which has 1 to 20 carbon atoms and which may have a substituent; the aliphatic group may contain one selected from the group consisting of —O—, —S—, —O—C(=O)—, —C(=O)—O—, —O—C(=O)—O—, —NR$^4$—C(=O)—, —C(=O)—NR$^4$—, —NR$^4$— and —C(=O)—, except the case where two or more adjacent —O— and two or more adjacent —S— are contained in the aliphatic group; and R$^4$ is a hydrogen atom or an alkyl group having 1 to 6 carbon atoms;

wherein Z1 and Z2 are each independently an alkenyl group which has 2 to 10 carbon atoms and which may be substituted by a halogen atom;

wherein Q1 to Q4 are each independently a hydrogen atom or an alkyl group which has 1 to 6 carbon atoms and which may have a substituent;

wherein A1 to A6 are each independently a divalent organic group having 1 to 30 carbon atoms; and wherein a and b are each independently 0 or 1.

(2) The left-handed-helix-inducing polymerizable chiral compound according to (1), wherein A1 to A6 of the formula (I) are each independently a phenylene group which may have a substituent, a biphenylene group which may have a substituent, or a naphthylene group which may have a substituent.

(3) The left-handed-helix-inducing polymerizable chiral compound according to (1) or (2), wherein Z1 and Z2 of the formula (I) are each independently one selected from the group consisting of CH$_2$=CH—, CH$_2$=C(CH$_3$)—, CH$_2$=C(Cl)—, CH$_2$=CH—CH$_2$—, CH$_2$=C(CH$_3$)—CH$_2$—, CH$_2$=C(CH$_3$)—CH$_2$CH$_2$—, (CH$_3$)$_2$C=CH—CH$_2$—, CH$_3$—CH=CH— and CH$_3$—CH=CH—CH$_2$—.

(4) The left-handed-helix-inducing polymerizable chiral compound according to any one of (1) to (3), in the formula (I), wherein Y1 to Y6 are each independently —C(=O)—O—, —O—C(=O)— or —O—;

wherein Yx and Yz are each —C(=O)—;

wherein G1 and G2 are each independently —(CH$_2$)$_6$— or —(CH$_2$)$_4$—, in both of which —O—, —C(=O)—O— or —O—C(=O)— may be contained;

wherein Z1 and Z2 are each independently CH$_2$=CH—, CH$_2$=C(CH$_3$)— or CH$_2$=C(Cl)—; and wherein A1 to A6 are each independently any one of groups represented by the following (A-i), (A-ii) and (A-iii):

[Chemical Formula 4]

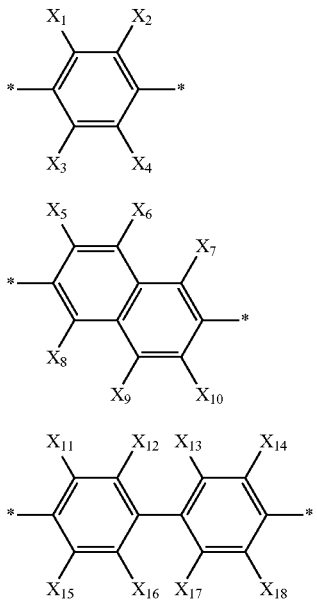

wherein * represents a bond; $X_1$ to $X_{18}$ are each independently one selected from the group consisting of a hydrogen atom, a halogen atom, an alkyl group which has 1 to 10 carbon atoms and which may have a substituent, a cyano group, a nitro group, $-OR^5$, $-O-C(=O)-R^5$, $-C(=O)-OR^5$, $-O-C(=O)-OR^5$, $-NR^6-C(=O)-R^5$, $-C(=O)-N(R^5)R^6$ and $-O-C(=O)-N(R^5)R^6$; $R^5$ and $R^6$ are each independently a hydrogen atom or an alkyl group which has 1 to 10 carbon atoms and which may have a substituent; with the provision that if $R^5$ and/or $R^6$ is an alkyl group, the alkyl group may contain one selected from the group consisting of $-O-$, $-S-$, $-O-C(=O)-$, $-C(=O)-O-$, $-O-C(=O)-O-$, $-NR^7-C(=O)-$, $-C(=O)-NR^7-$, $-NR^7-$ and $-C(=O)-$, except the case where two or more adjacent $-O-$ and two or more adjacent $-S-$ are contained in the alkyl group; and $R^7$ is a hydrogen atom or an alkyl group having 1 to 6 carbon atoms.

(5) The left-handed-helix-inducing polymerizable chiral compound according to any one of (1) to (4), in the formula (I), wherein Y1 to Y6 are each independently $-C(=O)-O-$, $-O-C(=O)-$ or $-O-$;

wherein Yx and Yz are each $-C(=O)-$;

wherein G1 and G2 are each independently $-(CH_2)_6-$ or $-(CH_2)_4-$;

wherein Z1 and Z2 are each independently $CH_2=CH-$ or $CH_2=C(CH_3)-$; and wherein A1 to A6 are each independently a group represented by the following (A-i) or (A-ii):

[Chemical Formula 5]

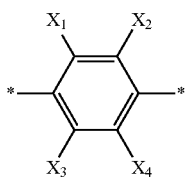

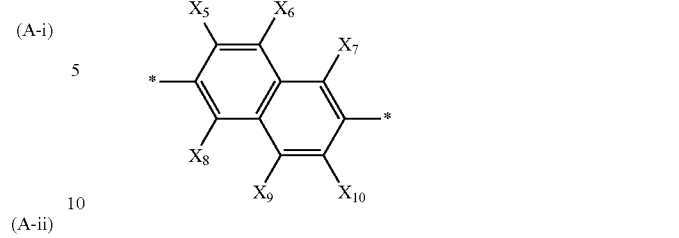

wherein * represents a bond; $X_1$ to $X_{10}$ are each independently one selected from the group consisting of a hydrogen atom, a halogen atom, an alkyl group which has 1 to 10 carbon atoms and which may have a substituent, a cyano group, a nitro group, $-OR^5$, $-O-C(=O)-R^5$, $-C(=O)-OR^5$, $-O-C(=O)-OR^5$, $-NR^6-C(=O)-R^5$, $-C(=O)-N(R^5)R^6$ and $-O-C(=O)-N(R^5)R^6$; $R^5$ and $R^6$ are each independently a hydrogen atom or an alkyl group which has 1 to 10 carbon atoms and which may have a substituent; with the provision that if $R^5$ and/or $R^6$ is an alkyl group, the alkyl group may contain one selected from the group consisting of $-O-$, $-S-$, $-O-C(=O)-$, $-C(=O)-O-$, $-O-C(=O)-O-$, $-NR^7-C(=O)-$, $-C(=O)-NR^7-$, $-NR^7-$ and $-C(=O)-$, except the case where two or more adjacent $-O-$ and two or more adjacent $-S-$ are contained in the alkyl group; and $R^7$ is a hydrogen atom or an alkyl group having 1 to 6 carbon atoms.

(6) The left-handed-helix-inducing polymerizable chiral compound according to any one of (1) to (5), in the formula (I), wherein Y1 to Y6 each independently $-C(=O)-O-$, $-O-C(=O)-$ or $-O-$;

wherein Yx and Yz are each $-C(=O)-$;

wherein G1 and G2 are each independently $-(CH_2)_6-$ or $-(CH_2)_4-$;

wherein Z1 and Z2 are each independently $CH_2=CH-$;

wherein Q1 to Q4 are each independently a hydrogen atom or a methyl group;

wherein A1, A3, A4 and A6 are each independently a group represented by the following (A-i); and wherein A2 and A5 are each independently a group represented by the following (A-i) or (A-ii):

[Chemical Formula 6]

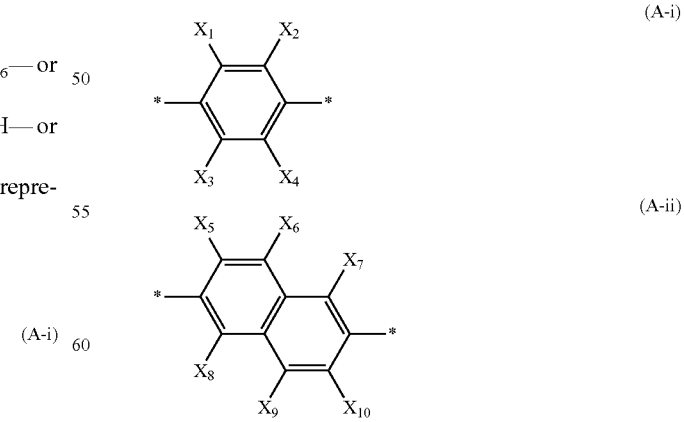

wherein * represents a bond; $X_1$ to $X_{10}$ are each independently one selected from the group consisting of a hydrogen atom, a halogen atom, an alkyl group which has 1 to 10 carbon atoms and which may have a substituent, a cyano group, a nitro group, —OR⁵, —O—C(=O)—R⁵ and —C(=O)—OR⁵; and R⁵ is a hydrogen atom or an alkyl group which has 1 to 10 carbon atoms and which may have a substituent.

(7) The left-handed-helix-inducing polymerizable chiral compound according to any one of (1) to (4), in the formula (I), wherein a=b=0, and G1 and G2 are each —CH₂CH₂C(=O)OCH₂CH₂— or —CH₂CH₂C(=O)CH₂CH₂—;

wherein A3 and A4 are each independently a group represented by the following (A-i); and wherein A2 and A5 are each independently a group represented by the following (A-i) or (A-ii):

[Chemical Formula 7]

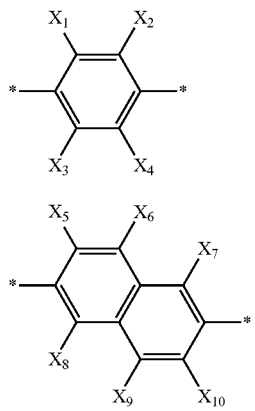

wherein * represents a bond; $X_1$ to $X_{10}$ are each independently one selected from the group consisting of a hydrogen atom, a halogen atom, an alkyl group which has 1 to 10 carbon atoms and which may have a substituent, a cyano group, a nitro group, —OR⁵, —O—C(=O)—R⁵ and —C(=O)—OR⁵; and R⁵ is a hydrogen atom or an alkyl group which has 1 to 10 carbon atoms and which may have a substituent.

Second, the present invention provides the following left-handed helical, polymerizable liquid crystal composition (8).

(8) A left-handed helical, polymerizable liquid crystal composition comprising at least any one of the polymerizable chiral compounds defined by (1) to (7) and at least one kind of polymerizable liquid crystal compound.

Third, the present invention provides the following left-handed helical liquid crystal polymer (9).

(9) A left-handed helical liquid crystal polymer obtained by polymerization of the left-handed helical, polymerizable liquid crystal composition defined by (8).

Fourth, the present invention provides the following optically anisotropic body (10).

(10) An optically anisotropic body comprising the left-handed helical liquid crystal polymer defined by (9) as a constitutional material.

Advantageous Effects of Invention

The present invention provides a left-handed-helix-inducing polymerizable chiral compound with excellent solubility and compatibility, a left-handed helical polymerizable liquid crystal composition, a left-handed helical liquid crystal polymer with high helical twisting power (HTP), and an optically anisotropic body comprising the left-handed helical liquid crystal polymer of the present invention as a constitutional material.

DESCRIPTION OF EMBODIMENTS

Hereinafter, the present invention will be explained in detail under (1) left-handed-helix-inducing polymerizable chiral compound, (2) left-handed helical polymerizable liquid crystal composition, (3) left-handed helical liquid crystal polymer and (4) optically anisotropic body.

(1) Left-Handed-Helix-Inducing Polymerizable Chiral Compound

The left-handed-helix-inducing polymerizable chiral compound (hereinafter may be referred to as "polymerizable chiral compound") of the present invention is a compound represented by the above formula (I). "Left-handed-helix-inducing" means having a property of exhibiting a left-handed helical cholesteric phase when mixed with a polymerizable liquid crystal compound.

In the formula (I), X represents the following formula (X-i) or (X-ii). Due to offering larger helical twisting power (HTP), the formula (X-ii) is preferred.

[Chemical Formula 8]

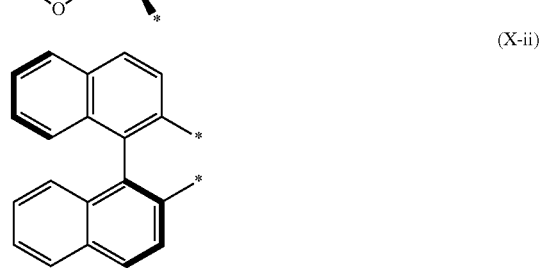

wherein * represents a bond.

In the formula (I), Y1 to Y6 are each independently one selected from the group consisting of a chemical single bond, —O—, —S—, —O—C(=O)—, —C(=O)—O—, —O—C(=O)—O—, —NR¹—C(=C)—, —C(=O)—NR¹—, —O—C(=O)—NR¹—, —NR¹—C(=O)—O—, —NR¹—C(=O)—NR¹—, —O—NR¹— and —NR¹—O—.

Among them, —O—, —O—C(=O)— and —C(=O)—O— are preferred.

R¹ is a hydrogen atom or an alkyl group having 1 to 6 carbon atoms such as a methyl group, an ethyl group, an n-propyl group, an isopropyl group, an n-butyl group, an isobutyl group, a sec-butyl group, a t-butyl group, an n-pentyl group, an isopentyl group, a neopentyl group or an n-hexyl group. Among them, R¹ is preferably a hydrogen atom or a methyl group.

Yx is one selected from the group consisting of a chemical single bond, —C(=O)—, —O—C(=O)—, —NR²—C(=O)—, —CH=CH—C(=O)—, —CH₂—, —C₂H₄— and —CF₂—.

Yz is one selected from the group consisting of a chemical single bond, —C(=O)—, —C(=O)—O—, —C(=O)—NR³—, —C(=O)—CH=CH—, —CH₂—, —C₂H₄— and —CF₂—.

Like $R^1$, $R^2$ and $R^3$ are each a hydrogen atom or an alkyl group having 1 to 6 carbon atoms.

G1 and G2 are each independently a divalent aliphatic group which has 1 to 20 carbon atoms and which may have a substituent.

The divalent aliphatic group having 1 to 20 carbon atoms as G1 and G2 can be a chain aliphatic group or an aliphatic group having an alicyclic structure. Among chain aliphatic groups and aliphatic groups having an alicyclic structure, from the viewpoint of exerting the desired effects of the present invention more effectively, preferred is an aliphatic group which has 1 to 12 carbon atoms and which may have a substituent. More preferred are chain aliphatic groups such as an alkylene group having 1 to 20 carbon atoms and an alkenylene group having 2 to 20 carbon atoms. Still more preferred are alkylene groups having 1 to 12 carbon atoms, such as a methylene group, an ethylene group, a trimethylene group, a propylene group, a betramethylene group, a pentamethylene group, a hexamethylene group and an octamethylene group. Particularly preferred is a hexamethylene group ($-(CH_2)_6-$).

Examples of the substituent of the aliphatic group as G1 and G2 include halogen atoms such as a fluorine atom, a chlorine atom, a bromine atom and an iodine atom, and alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group and an n-hexyloxy group. Among them, preferred are a fluorine atom, a methoxy group and an ethoxy group.

The aliphatic group may contain one selected from the group consisting of $-O-$, $-S-$, $-O-C(=O)-$, $-C(=O)-O-$, $-O-C(=O)-O-$, $-NR^4-C(=O)-$, $-C(=O)-NR^4-$, $-NR^4-$ and $-C(=O)-$, except the case where two or more adjacent $-O-$ and two or more adjacent $-S-$ are contained in the aliphatic group. Among them, preferred are $-O-$, $-O-C(=O)-$, $-C(=O)-O-$ and $-C(=O)-$.

Like $R^1$, $R^4$ is a hydrogen atom or an alkyl group having 1 to 6 carbon atoms. $R^4$ is preferably a hydrogen atom or a methyl group.

Specific examples of the aliphatic group containing the above groups include $-CH_2-CH_2-O-CH_2-CH_2-$, $-CH_2-CH_2-S-CH_2-CH_2-$, $-CH_2-CH_2-O-C(=O)-CH_2-CH_2-$, $-CH_2-CH_2-C(=O)-O-CH_2-$, $-CH_2-O-C(=O)-CH_2-CH_2-$, $-CH_2-CH_2-NR^4-C(=O)-CH_2-CH_2-$, $-CH_2-CH_2-C(=O)-NR^4-CH_2-$, $-CH_2-NR^4-CH_2-CH_2-$ and $-CH_2-C(=O)-CH_2-$.

Z1 and Z2 are each independently an alkenyl group which has 2 to 10 carbon atoms and which may be substituted by a halogen atom.

The alkenyl group as Z1 and Z2 which has 2 to 10 carbon atoms and which may be substituted by a halogen atom, is preferably an alkenyl group having 2 to 6 carbon atoms. Examples of the halogen atom (substituent) include a fluorine atom, a chlorine atom and bromine atom, and preferred is a chlorine atom.

Specific examples of the alkenyl group as Z1 and Z2 which has 2 to 10 carbon atoms and which may be substituted by a halogen atom, include $CH_2=CH-$, $CH_2=C(CH_3)-$, $CH_2=C(Cl)-$, $CH_2=CH-CH_2-$, $CH_2=C(CH_3)-CH_2-$, $CH_2=C(CH_3)-CH_2CH_2-$, $(CH_3)_2C=CH-CH_2-$, $CH_3-CH=CH-$, $CH_3-CH=CH-CH_2-$, $CH_2=CH-CH_2-CH_2-$ and $(CH_3)_2C=CH-CH_2-$.

Among them, from the viewpoint of exerting the desired effects of the present invention more effectively, preferred are $CH_2=CH-$, $CH_2=C(CH_3)-$, $CH_2=C(Cl)-$, $CH_2=CH-CH_2-$, $CH_2=C(CH_3)-CH_2-$, $CH_2=C(CH_3)-CH_2CH_2-$, $(CH_3)_2C=CH-CH_2-$, $CH_3-CH=CH-$ and $CH_3-CH=CH-CH_2-$. More preferred are $CH_2=CH-$ and $CH_2=C(CH_3)-$, and still more preferred is $CH_2=CH-$.

Q1 to Q4 are each independently a hydrogen atom or, like $R^1$, an alkyl group which has 1 to 6 carbon atoms and which may have a substituent. Among them, preferably, Q1 to Q4 are each independently a hydrogen atom or methyl group, and more preferably a hydrogen atom.

A1 to A6 are each independently a divalent organic group A having 1 to 30 carbon atoms. The organic group A preferably has 6 to 30 carbon atoms, more preferably 6 to 20 carbon atoms.

The organic group A is not particularly limited; however, it is preferably one having an aromatic group.

Examples of the one having an aromatic group include a divalent hydrocarbon group containing one or more monocyclic aromatic hydrocarbons having one benzene ring (e.g., benzene, toluene, xylene) and a divalent hydrocarbon group containing a polycyclic aromatic hydrocarbon having two or more (generally two to four) benzene rings (e.g., naphthalene, biphenyl, terphenyl).

Among them, preferably, A1 to A6 are each independently a phenylene group which may have a substituent, a naphthylene group which may have a substituent, or a biphenylene group which may have a substituent. More preferably, A1 to A6 are each independently any one of groups represented by the following (A-i), (A-ii) and (A-iii). Still more preferably, A1 to A6 are each independently a group represented by (A-i) or (A-ii). Particularly preferably, A1, A3, A4 and A6 are each independently a group represented by the following (A-i), and A2 and A5 are each independently a group represented by the following (A-i) or (A-ii):

[Chemical Formula 9]

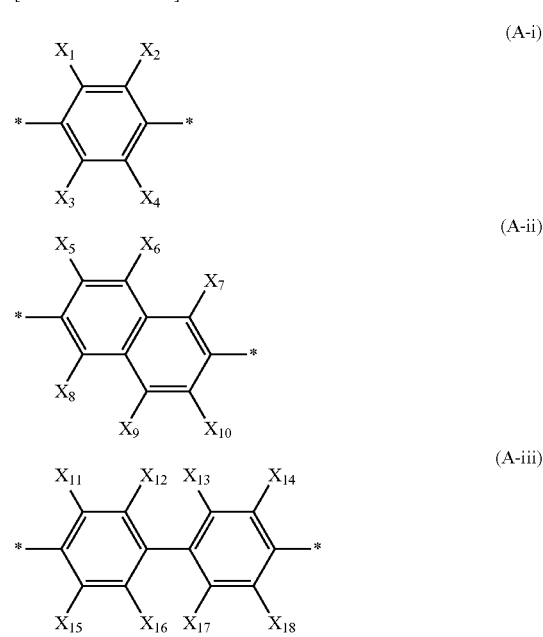

wherein * represents a bond; $X_1$ to $X_{18}$ are each independently one selected from the group consisting of a hydrogen atom, a halogen atom, an alkyl group which has 1 to 10 carbon atoms and which may have a substituent, a cyano group, a nitro group, —$OR^5$, —O—C(=O)—$R^5$, —C(=O)—$OR^5$, —O—C(=O)—$OR^5$, —$NR^6$—C(=O)—$R^5$, —C(=O)—N($R^5$)$R^6$ and —O—C(=O)—N($R^5$)$R^6$.

$R^5$ and $R^6$ are each independently a hydrogen atom or an alkyl group which has 1 to 10 carbon atoms and which may have a substituent.

Examples of the alkyl group as $R^5$ and $R^6$ which has 1 to 10 carbon atoms and which may have a substituent, include a methyl group, an ethyl group, an n-propyl group, an isopropyl group, an n-butyl group, an s-butyl group, an isobutyl group, a t-butyl group, an n-pentyl group, an n-hexyl group, an n-heptyl group, an n-octyl group, an n-nonyl group and an n-decyl group. Preferred are a methyl group, an ethyl group, an n-propyl group and an isopropyl group.

Examples of the substituent of the alkyl group which has 1 to 10 carbon atoms and which may have a substituent, include halogen atoms such as a fluorine atom, a chlorine atom, a bromine atom and an iodine atom, and alkoxy groups having 1 to 6 carbon atoms, such as a methoxy group, an ethoxy group, an n-propoxy group, an isopropoxy group, an n-butoxy group, a sec-butoxy group, a t-butoxy group, an n-pentyloxy group and an n-hexyloxy group.

With the provision that if $R^5$ and/or $R^6$ is an alkyl group, the alkyl group may contain one selected from the group consisting of —O—, —S—, —O—C(=O)—, —C(=O)—O—, —O—C(=O)—O—, —$NR^7$—C(=O)—, —C(=O)—$NR^7$—, —$NR^7$— and —C(=O)—, except the case where two or more adjacent —O— and two or more adjacent —S— are contained in the alkyl group.

$R^7$ is a hydrogen atom or, like $R^1$, an alkyl group having 1 to 6 carbon atoms.

In the formula (I), a and b are each independently 0 or 1. From the viewpoint of ease of synthesis, both of a and b are preferably 0 or 1. From the viewpoint of left-handed helical twisting power, both of a and b are more preferably 1.

The polymerizable chiral compound of the present invention is preferably a compound (α) described below. Among the compounds (α), a compound (β) and a compound (ε) are more preferred, which are described below. Among the compounds (β), a compound (γ) is still more preferred, which is described below.

(α) A compound represented by the formula (I),
wherein Y1 to Y6 are each independently —C(=O)—O—, —O—C(=O)— or —O—;
wherein Yx and Yz are each —C(=O)—;
wherein G1 and G2 are each independently —$(CH_2)_6$— or —$(CH_2)_4$—, in both of which —O—, —C(=O)—O— or —O—C(=O)— may be contained;
wherein Z1 and Z2 are each independently $CH_2$=CH—, $CH_2$=C($CH_3$)— or $CH_2$=C(Cl)—; and
wherein A1 to A6 are each independently any one of groups represented by the above (A-i), (A-ii) and (A-iii).

(β) A compound represented by the formula (I),
wherein Y1 to Y6 are each independently —C(=O)—O—, —O—C(=O)— or —O—;
wherein Yx and Yz are each —C(=O)—;
wherein G1 and G2 are each independently —$(CH_2)_6$— or —$(CH_2)_4$—;
wherein Z1 and Z2 are each independently $CH_2$=CH— or $CH_2$=C($CH_2$)—; and
wherein A1 to A6 are each independently a group represented by the above (A-i) or (A-ii).

(γ) A compound represented by the formula (I),
wherein Y1 to Y6 each independently —C(=O)—O—, —O—C(=O)— or —O—;
wherein Yx and Yz are each —C(=O)—;
wherein G1 and G2 are each independently —$(CH_2)_6$— or —$(CH_2)_4$—;
wherein Z1 and Z2 are each independently $CH_2$=CH—;
wherein Q1 to Q4 are each independently a hydrogen atom or a methyl group;
wherein A1, A3, A4 and A6 are each independently a group represented by the above (A-i); and
wherein A2 and A5 are each independently a group represented by the above (A-i) or (A-ii).

(ε) A compound represented by the formula (I),
wherein a=b=0, and G1 and G2 are each —$CH_2CH_2$C(=O)O$CH_2CH_2$— or —$CH_2CH_2$OC(=O)$CH_2CH_2$—;
wherein A3 and A4 are each independently a group represented by the above (A-i); and
wherein A2 and A5 are each independently a group represented by the above (A-i) or (A-ii).

The polymerizable chiral compound of the present invention has excellent solubility and compatibility. As described below, it exhibits a left-handed helical cholesteric phase when mixed with a polymerizable liquid crystal compound.

Any of the polymerizable chiral compounds of the present invention can be produced by a combination of known methods for forming various kinds of chemical bonds such as —O—, —S—, —NH—C(=O)—, —C(=O)—NH—, —NH—C(=O)—NH—, —O—C(=O)— and —C(=O)—O— (for example, see Sandler & Karo, Syntheses of Organic compounds Classified by Functional Group, Vol. I and Vol. II, Hirokawa Shoten, Tokyo (1976)).

Typically, the polymerizable chiral compound of the present invention can be produced by appropriately bonding and modifying known compounds with desired structures by optionally combining an ether bond (—O—)-forming reaction, an ester bond (—C(=O)—O—)-forming reaction, an amide bond (—C(=O)NH—)-forming reaction and an acid chloride (—COCl)-forming reaction.

Ether bond formation can be carried out by the following methods, for example.

(i) A compound described by the formula D1-hal (hal represents a halogen atom, and this is the same in the following methods) and a compound described by the formula D2-OMet (Met represents an alkali metal (mainly sodium) and this is the same in the following methods) are mixed and condensed. In these formulae, each of D1 and D2 represents an optional organic group B (this is the same in the following methods). This reaction is generally called the Williamson synthesis.

(ii) A compound described by the formula D1-hal and a compound described by the formula D2-OH are mixed and condensed in the presence of a base such as sodium hydroxide or potassium hydroxide.

(iii) A compound described by the formula D1-E (E represents an epoxy group) and a compound described by the formula D2-OH are mixed and condensed in the presence of a base such as sodium hydroxide or potassium hydroxide.

(iv) A compound described by the formula D1-OFN (OFN represents a group having an unsaturated bond) and a compound described by the formula D2-OMet are mixed to initiate an addition reaction in the presence of a base such as sodium hydroxide or potassium hydroxide.

(v) A compound described by the formula D1-hal and a compound described by the formula D2-OMet are mixed and condensed in the presence of copper or copper(I) chloride. This reaction is generally called the Ullmann condensation.

Ester bond and amide bond formation can be carried out by the following methods, for example.

(vi) A compound described by the formula D1-COOH and a compound described by the formula D2-OH or D2-$NH_2$ are subjected to dehydration condensation in the presence of a dehydration-condensation agent (e.g., N,N-dicyclohexylcarbodiimide).

(vii) A compound described by the formula D1-CO-hal is obtained by the action of a halogenating agent on a compound described by the formula D1-COOH. The thus-obtained compound and a compound described by the formula D2-OH or D2-NH$_2$ are reacted in the presence of a base.

(viii) A mixed acid anhydride is obtained by the action of an acid anhydride on a compound described by the formula D1-COOH. The thus-obtained mixed acid anhydride is reacted with a compound described by the formula D2-OH or D2-NH$_2$.

(ix) A compound described by the formula D1-COOH and a compound described by the formula D2-OH or D2-NH$_2$ are subjected to dehydration condensation in the presence of an acid catalyst or base catalyst.

Acid chloride formation can be carried out by the following methods, for example.

(x) By the action of phosphorous trichloride or phosphorous pentachloride on a compound described by the formula D1-COOH.

(xi) By the action of thionyl chloride on a compound described by the formula D1-COOH.

(xii) By the action of oxalyl chloride on a compound described by the formula D1-COOH.

(xiii) By the action of chlorine on a compound described by the formula D1-COOAg (Ag: silver).

(xiv) By the action of a carbon tetrachloride solution of red mercury(II) oxide on a compound described by the formula D1-COOH.

In the production of the polymerizable chiral compound of the present invention (particularly in the production of a polymerizable chiral compound having an asymmetric structure), it is sometimes possible to facilitate the synthesis by protecting a hydroxyl group that is present in an intermediate, and thus the yield can be increased.

There are known methods that can be used to protect the hydroxyl group (for example, see Greene's Protective Groups in Organic Synthesis, 3$^{rd}$ Edition, published by Wiley-Interscience (1999)).

The hydroxyl group can be protected by the following methods, for example.

(xv) A compound described by the formula D1D2D3-Si-hal is mixed and reacted with a compound described by the formula D4-OH in the presence of a base such as imidazole or pyridine. In the formulae, each of D3 and D4 represents an optional organic group B (this is the same in the following methods.)

(xvi) A vinyl ether such as 3,4-dihydro-2H-pyran is mixed and reacted with a compound described by the formula D2-OH in the presence of an acid such as p-toluenesulfonic acid, pyridinium p-toluenesulfonate or hydrogen chloride.

(xvii) A compound described by the formula D1-C(=O)-hal is mixed and reacted with a compound described by the formula D4-OH in the presence of a base such as triethylamine or pyridine.

(xviii) An acid anhydride described by the formula D1-C(=O)—O—C(=O)-D2 is mixed and reacted with a compound described by the formula D3-OH, or they are mixed and reacted in the presence of a base such as sodium hydroxide or triethylamine.

(xix) A compound described by the formula D1-hal is mixed and reacted with a compound described by the formula D2-OH in the presence of a base such as sodium hydroxide or triethylamine.

(xx) A compound described by the formula D1-O—CH$_2$-hal is mixed and reacted with a compound described by the formula D2-OH in the presence of a base such as sodium hydride, sodium hydroxide, triethylamine or pyridine.

(xxi) A compound described by the formula D1-O—CH$_2$—C(=O)-hal is mixed and reacted with a compound described by the formula D2-OH in the presence of a base such as potassium carbonate or sodium hydroxide.

(xxii) A compound described by the formula D1-O—C(=O)-hal is mixed and reacted with a compound described by the formula D2-OH in the presence of a base such as triethylamine or pyridine.

Deprotection can be performed by the following known methods, depending on the structure and type of the protecting group.

(xxiii) Deprotection by mixing with a fluoride ion such as tetrabutylammonium fluoride.

(xxiv) Deprotection by mixing in the presence of an acid such as p-toluenesulfonic acid, pyridinium p-toluenesulfonate, hydrogen chloride or acetic acid.

(xxv) Deprotection by mixing in the presence of a base such as sodium hydride, sodium hydroxide, potassium hydroxide, sodium carbonate, potassium carbonate, triethylamine or pyridine.

(xxvi) Deprotection by hydrogenation in the presence of a catalyst such as Pd—C.

In particular, the polymerizable chiral compound of the present invention can be obtained as follows, for example.

[Chemical Formula 10]

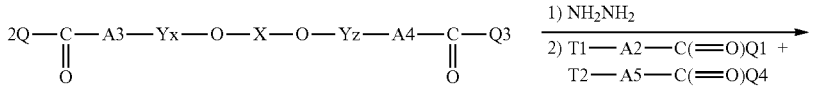

(2)

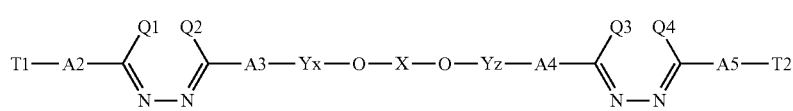

(3)

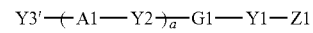

(4a)

+

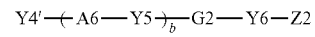

(4b)

-continued

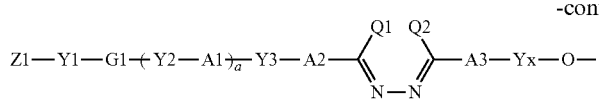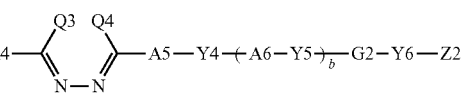

wherein each of A1 to A6, X, Y1 to Y6, Yx, Yz, Q1 to Q4, G1, G2, Z1, Z2, a and b represents the same meaning as above; T1 represents a group that reacts with Y3' to produce Y3; and T2 represents a group that reacts with Y4' to produce Y4. For example, in the case where T1 and T2 are each a hydroxyl group (OH) and Y3' and Y4' are each a carboxyl group (COOH), T1 reacts with Y3' to produce Y3 [—C(=O)—O—] and T2 reacts with Y4' to produce Y4 [—O—C(=O)—].

In particular, the compound represented by the formula (2) is reacted with hydrazine (or hydrazine monohydrate) and then with the compounds described by the formulae T1-A2-C(=O)Q1 and T2-A5-C(=O)Q4 to obtain an intermediate represented by the formula (3) (step 1). Next, the thus-obtained intermediate is reacted with compounds represented by the formulae (4a) and (4b) (step 2), thereby obtaining the target compound represented by the formula (I) (the polymerizable chiral compound of the present invention).

(=O)Q1 and T2-A5-C(=O)Q4 represent the same compound, the compound can be used in an amount of 2 to 10 moles or more.

The reaction in the step 1 proceeds smoothly in the temperature range of −10° C. to the boiling point of the solvent.

The reaction time depends on the reaction scale but is generally several minutes to several hours.

A reaction solution containing the compound represented by the formula (3) is obtained in the manner as described above.

In the present invention, the compound represented by the formula (3) can be separated from the reaction solution and used in the next step 2, or the reaction solution containing the compound represented by the formula (3) can be used as it is in the step 2, without separating the compound represented by the formula (3).

The compound represented by the formula (3) can be also produced by the following method.

[Chemical Formula 11]

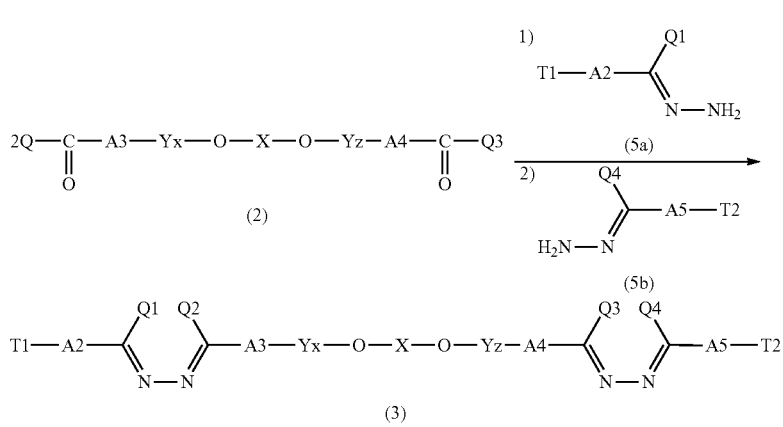

The step 1 can be carried out in an appropriate organic solvent.

Examples of the organic solvent to be used include alcohol solvents such as methanol, ethanol, n-propanol, isopropanol and n-butanol; ether solvents such as diethyl ether, tetrahydrofuran, 1,2-dimethoxyethane and 1,4-dioxane; ester solvents such as ethyl acetate, propyl acetate and methyl propionate; aromatic hydrocarbon solvents such as benzene, toluene and xylene; aliphatic hydrocarbon solvents such as n-pentane, n-hexane and n-heptane; amide solvents such as N,N-dimethylformamide, N-methylpyrrolidone and hexamethylphosphoric triamide; sulfur-containing solvents such as dimethylsulfoxide and sulfolane; and mixed solvents comprising two or more of the above solvents.

In the step 1, the used amount of hydrazine is generally 2 to 10 moles with respect to 1 mole of the compound represented by the formula (2).

Each of the used amounts of the compounds described by the formulae T1-A2-C(=O)Q1 and T2-A5-C(=O)Q4 is generally 1 to 5 moles with respect to 1 mole of the compound represented by the formula (2). If the formulae T1-A2-C wherein each of A2 to A5, X, Yx, Yz, Q1 to Q4, T1 and T2 represents the same meaning as above.

In particular, the compound represented by the formula (2) is reacted with the compound represented by the formula (5a) and then with the compound represented by the formula (5b) consecutively, thereby obtaining the compound represented by the formula (3).

The compound represented by the formula (5a) can be produced by the reaction of hydrazine with the compound described by the formula T1-A2-C(=O)Q1. The compound represented by the formula (5b) can be produced by the reaction of hydrazine with the compound described by the formula T2-A5-C(=O)Q4.

Next, the compound represented by the formula (3) is reacted with the compounds represented by the formulae (4a) and (4b) (step 2), thereby obtaining the target compound represented by the formula (I) (the polymerizable chiral compound of the present invention).

Preferred specific examples of the compounds represented by the formulae (4a) and (4b) include the following compounds. The present invention is not limited to the following compounds, however.

[Chemical Formula 12]

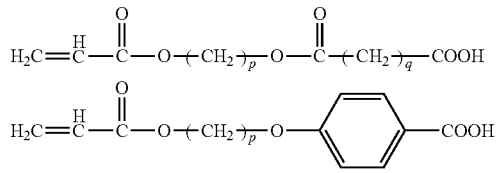

wherein p and q are each independently an integer of 1 to 6.

The step 2 can be carried out in an appropriate organic solvent.

Examples of the organic solvent include organic solvents that are the same as those listed in the step 1.

In the step 2, each of the used amounts of the compounds represented by the formulae (4a) and (4b) is generally 1 to 3 moles with respect to 1 mole of the compound represented by the formula (3).

If the formulae (4a) and (4b) represent the same compound, the compound can be used in an amount of 2 to 6 moles or more.

The reaction in the step 2 proceeds smoothly in the temperature range of $-10°$ C. to the boiling point of the solvent.

The reaction time depends on the reaction scale but is generally several minutes to several hours.

A post treatment which is usual in synthetic organic chemistry is performed after the reaction, and as needed, a known separation and purification process such as column chromatography, recrystallization method or distillation is performed, thereby separating the target compound.

The structure of the target compound can be identified by NMR spectrum measurement, IR spectrum measurement, mass spectrum measurement, elemental analysis or the like.

The compound represented by the formula (2), which is a starting material, can be produced as follows:

[Chemical Formula 13]

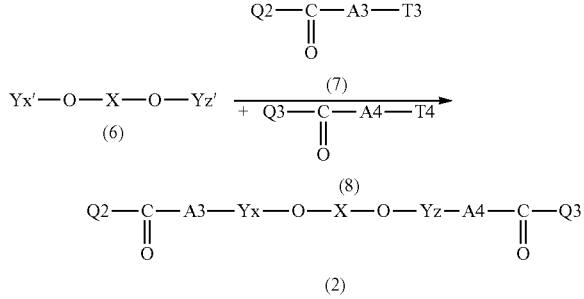

wherein each of A3, A4, X, Yx, Yz, Q2 and Q3 represents the same meaning as above; T3 represents a group that reacts with Yx' to produce Yx; and T4 represents a group that reacts with Yz' to produce Yz.

In particular, the compound represented by the formula (6), which will be a chiral group, is reacted with the compounds represented by the formulae (7) and (8), thereby obtaining the target compound represented by the formula (2).

Preferred specific examples of the compound represented by the formula (6) include the following compounds.

[Chemical Formula 14]

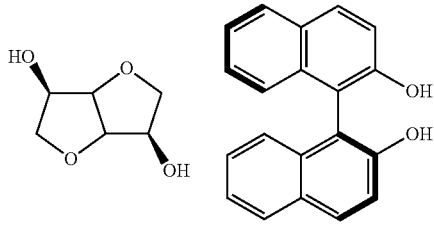

Preferred specific examples of the compounds represented by the formulae (7) and (8) include the following compounds. The present invention is not limited to the following compounds, however.

[Chemical Formula 15]

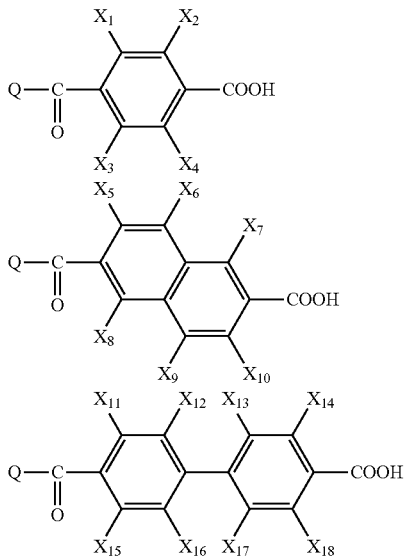

wherein each of $X_1$ to $X_{18}$ represents the same meaning as above; and Q is Q2 or Q3.

Many of the above compounds are known substances and can be produced by known methods.

(2) Left-Handed Helical, Polymerizable Liquid Crystal Composition

The left-handed helical, polymerizable liquid crystal composition of the present invention (hereinafter may be referred to as "polymerizable liquid crystal composition") comprises at least one kind of the polymerizable chiral compounds of the present invention and at least one polymerizable liquid crystal compound.

The polymerizable liquid crystal compound comprising the polymerizable liquid crystal composition of the present invention exhibits a left-handed helical cholesteric phase when mixed with the polymerizable chiral compound of the present invention.

The polymerizable liquid crystal compound used for the polymerizable liquid crystal composition of the present invention is a liquid crystal compound which is polymerizable. Specific examples thereof include compounds disclosed in Japanese Patent Application Laid-Open (JP-A) No. H11-130729, JP-A No. H08-104870, JP-A No. 2005-309255, JP-A No. 2005-263789, Japanese translation of PCT international application No. 2002-533742, JP-A No. 2002-308832, JP-A No. 2002-265421, JP-A No. S62-070406, JP-A No. H11-100575, International Publication No. WO08/133,290 pamphlet, JP-A No. 2008-291218, JP-A No. 2009-167378, and Japanese Patent Application No. 2008-170835. In the present invention, the compound disclosed in JP-A No. 2008-291218 is preferred.

In the present invention, it is possible to use one kind of polymerizable liquid crystal compound alone or two or more kinds of polymerizable liquid crystal compounds in combination.

In the polymerizable liquid crystal composition of the present invention, the compounding ratio of the polymerizable chiral compound is generally 0.1 to 100 parts by mass, preferably 0.5 to 10 parts by mass, more preferably 1 to 8 parts by mass, with respect to 100 parts by mass of the polymerizable liquid crystal compound.

In the polymerizable liquid crystal composition of the present invention, a polymerizable non-liquid crystal compound may be also contained, in addition to the polymerizable liquid crystal compound.

The polymerizable non-liquid crystal compound is added in order to control the phase transition temperature of the left-handed helical liquid crystal polymer to be obtained.

A polymerizable non-liquid crystal compound is generally a polymerizable monomer and no liquid crystal polymer is obtained even when the polymerizable non-liquid crystal compound itself is polymerized.

The polymerizable non-liquid crystal compound is not particularly limited; however, from the viewpoint of achieving the purposes of the present invention, the compound represented by the following formula is preferred:

[Chemical Formula 16]

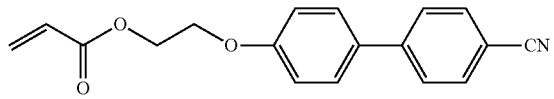

In the case of using the polymerizable non-liquid crystal compound, the compounding amount is preferably, in the mass ratio, polymerizable liquid crystal compound:polymerizable non-liquid crystal compound=60:40 to 95:5, preferably 70:30 to 90:10.

In general, the polymerizable liquid crystal composition of the present invention preferably comprises a polymerization initiator.

As the polymerization initiator, an appropriate polymerization initiator can be selected for use, according to the type of a polymerizable group that is present in the polymerizable liquid crystal compound. For example, when the polymerizable group is a radically polymerizable group, a radical polymerization initiator can be used. When the polymerizable group is an anionically polymerizable group, an anionic polymerization initiator can be used. When the polymerizable group is a cationically polymerizable group, a cationic polymerization initiator can be used.

As the radical polymerization initiator, a thermal radical generator or photo radical generator can be used. Suitably used is a photo radical generator.

Examples of the photo radical generator include benzoins such as benzoin, benzoin methyl ether and benzoin propyl ether; acetophenones such as acetophenone, 2,2-dimethoxy-2-phenylacetophenone, 2,2-diethoxy-2-phenylacetophenone, 1,1-dichloroacetophenone, 1-hydroxycyclohexylphenylketone, 2-methyl-1-[4-(methylthio)phenyl]-2-morpholino-propane-1-on and N,N-dimethylaminoacetophenone; anthraquinones such as 2-methylanthraquinone, 1-chloroanthraquinone and 2-amylanthraquinone; thioxanthones such as 2,4-dimethylthioxanthone, 2,4-diethylthioxanthone, 2-chlorothioxanthone and 2,4-diisopropylthioxanthone; ketals such as acetophenone dimethyl ketal and benzyl dimethyl ketal; benzophenones such as benzophenone, methylbenzophenone, 4,4-dichlorobenzophenone, 4,4-bisdiethylaminobenzophenone, Michler's ketone and 4-benzoyl-4-methyldiphenylsulfide; and 2,4,6-trimethylbenzoyldiphenylphosphineoxide.

Specific examples of the photo radical polymerization initiator include Irgacure 907, Irgacure 184, Irgacure 369, and Irgacure 651 (product names; manufactured by Chiba Specialty Chemicals, Inc.)

Examples of the anionic polymerization initiator include alkyllithium compounds; monolithium salts such as lithium biphenylide, lithium naphtalenide and lithium pyrenide; monosodium salts such as sodium biphenylide, sodium naphtalenide and sodium pyrenide; and multifunctional initiators such as dilithium salt or trilithium salt.

Examples of the cationic polymerization initiator include protonic acids such as sulfuric acid, phosphoric acid, perchloric acid and trifluoromethanesulfonic acid; Lewis acids such as boron trifluoride, aluminum chloride, titanium tetrachloride and tin tetrachloride; and aromatic onium salts and combinations of aromatic onium salts with a reducing agent.

These polymerization initiators can be used alone or in combination of two or more kinds.

In the polymerizable liquid crystal composition of the present invention, the compounding ratio of the polymerization initiator is generally 0.1 to 30 parts by mass, preferably 0.5 to 10 parts by mass, with respect to 100 parts by mass of the polymerizable liquid crystal compound.

When initiating (co)polymerization of the polymerizable liquid crystal compound (with other copolymerizable monomer or the like used as needed), a functional compound such as an ultraviolet absorbing agent, an infrared absorbing agent or an antioxidant can be used as needed.

The polymerizable liquid crystal composition of the present invention preferably comprises a surfactant to control surface tension. The surfactant is not particularly limited, and in general, it is preferably a nonionic surfactant. As the nonionic surfactant, commercial products can be used. An example is a nonionic surfactant which is an oligomer having a molecular weight of a few thousand, such as KH-40 (product name; manufactured by: AGC SEIMI Chemical Co., Ltd.)

In the polymerizable liquid crystal composition of the present invention, the compounding ratio of the surfactant is generally 0.01 to 10 parts by mass, preferably 0.1 to 2 parts by mass, with respect to 100 parts by mass of the polymerizable liquid crystal compound.

To use the polymerizable liquid crystal composition of the present invention as a material for polarizing films or alignment films, or as a printing ink, a coating material, a protecting film, etc., other additive(s) can be contained depending on the purpose in addition to the above components, such as other copolymerizable monomers mentioned below, a metal, a metal complex, a dye, a pigment, a fluorescent material, a phosphorescent material, a leveling agent, a thixotropic agent, a gelation agent, a polysaccharide, an ultraviolet absorbing agent, an infrared absorbing agent, an antioxidant, an ion-exchange resin, a metal oxide such as titanium oxide. In the polymerizable liquid crystal composition of the present invention, the compounding ratio of other additive(s) is generally 0.1 to 20 parts by mass, with respect to 100 parts by mass of the polymerizable liquid crystal compound.

In general, the polymerizable liquid crystal composition of the present invention can be prepared by dissolving, in an appropriate organic solvent, a polymerizable liquid crystal compound, the polymerizable chiral compound of the present invention, a photo polymerization initiator, a nonionic surfactant and, as needed, other additive(s), each of which is in a predetermined amount.

Examples of the organic solvent include ketones such as cyclopentanone, cyclohexanone and methyl ethyl ketone; ester acetates such as butyl acetate and amyl acetate; halogenated hydrocarbons such as chloroform, dichloromethane and dichloroethane; and ethers such as 1,2-dimethoxyethane, 1,4-dioxane, cyclopentyl methyl ether, tetrahydrofuran, tetrahydropyran and 1,3-dioxolan.

These organic solvents may be used alone or in combination of two or more kinds.

The polymerizable liquid crystal composition obtained in the manner as described above is, as discussed in more detail below, useful as a material for producing a left-handed helical (left-twisted) cholesteric liquid crystal layer and a left-handed helical (left-twisted) cholesteric liquid crystal polymer.

(3) Left-Handed Helical Liquid Crystal Polymer

The left-handed helical liquid crystal polymer (hereinafter may be referred to as "liquid crystal polymer") of the present invention is a polymer obtained by (co)polymerization of the polymerizable liquid crystal composition of the present invention.

Herein, "(co)polymerization" refers to a general (co)polymerization reaction and a chemical reaction in a broad sense, including a (co)crosslinking reaction.

The liquid crystal polymer of the present invention can be easily obtained by (co)polymerizing the polymerizable liquid crystal composition of the present invention which comprises a polymerization initiator. The liquid crystal polymer thus obtained is a left-handed helical cholesteric liquid crystal polymer. In the present invention, from the viewpoint of efficient (co)polymerization reaction, it is preferable to use a polymerization initiator as mentioned above, especially a photo polymerization initiator. Hereinafter, embodiments of using the polymerizable liquid crystal composition of the present invention will be described.

In particular, the liquid crystal polymer of the present invention can be obtained by applying the polymerizable liquid crystal composition of the present invention to, for example, a support having an alignment function so that the applied composition is uniformly aligned in the state of retaining a cholesteric phase, the support being obtained by an alignment treatment, and then polymerizing the applied composition.

As the support, it is possible to use a substrate comprising a known and conventional material, irrespective of organic or inorganic. Examples of the material of the substrate include polycycloolefin products such as ZEONEX and ZEONOR (registered trademarks; manufactured by: ZEON Corporation), ARTON (registered trademark; manufactured by: JSR Corporation) and APEL (registered trademark; manufactured by: Mitsui Chemicals, Inc.), polyethylene terephthalate, polycarbonate, polyimide, polyamide, polymethylmethacrylate, polystyrene, polyvinyl chloride, polytetrafluoroethylene, cellulose, cellulose triacetate, polyethersulfone, silicon, glass and calcite. The form of the substrate can be a plate form or curved form. Substrates comprising the above materials can have an electrode layer, an antireflection function and/or a reflection function, as needed.

In the above method, to form a uniformly aligned state, a thin polyimide film is useful in controlling the alignment state of the polymerizable liquid crystal compound, the film being one that is used for general twisted nematic (TN) elements and super twisted nematic (STN) elements and being able to provide a pretilt angle.

In general, when the liquid crystal compound contacts with the support having an alignment function, the liquid crystal compound is aligned on the surface of the support along the direction in which the support was aligned by the alignment treatment. The method for performing the alignment treatment on the surface of the support has a large influence on whether the liquid crystal compound is aligned with the surface of the support horizontally, obliquely or vertically.

For example, when an alignment film having a slight pretilt angle is provided on the support, which is used for in plane switching (IPS) type liquid crystal display elements, a polymerizable liquid crystal layer which is almost horizontally aligned, is obtained.

When an alignment film used for TN liquid crystal display elements is provided on the support, a polymerizable liquid crystal layer having a slightly tilted alignment is obtained. When an alignment film used for STN liquid crystal display elements is used, a polymerizable liquid crystal layer having a highly tilted alignment is obtained.

When the polymerizable liquid crystal composition of the present invention is brought into contact with the support having a pretilt angle and a horizontal alignment function, an optically anisotropic body having a tilted alignment is obtained, in which the angle of the composition is uniform or varied continuously in the range from the surface of the support to around air interface.

Also, a substrate on which regions in alignment directions that are different in a pattern are distributed, can be produced by, for example, a method for exposing an organic thin film having a functional group in a molecule thereof, the group being able to cause a photodimerization reaction, or an organic thin film having a photoisomerizable functional group in a molecule thereof (hereinafter, such organic films will be referred to as "photo-alignment film") to polarized or non-polarized light (photo-alignment method).

First, a support with uniform alignment is prepared by exposing a support having a photo-alignment film provided thereon to a light of a wavelength that is in the absorption band of the photo-alignment film. Then, the support is covered with a mask and exposed to a light in a different state from that of the light used in the first irradiation having the wavelength in the absorption wavelength of the photo-alignment film, such as a light in a different polarization state or a light having a different exposure angle and direction, so that only an exposed region has an alignment function that is different from that of a region subjected to the first exposure.

The polymerizable liquid crystal composition is brought into contact with the above-obtained support on which regions with alignment functions that are different in a pattern are distributed; therefore, on the support, regions which are in alignment directions that are different in a pattern corresponding to the alignment functions of the support, are distributed. When the polymerization by exposure to light is performed on the substrate in this state, a liquid crystal polymer film having an alignment pattern is obtained.

Especially by using, as the above-described support, a support having an almost horizontal alignment function on which regions which are in alignment directions that are different in a pattern are distributed, a liquid crystal polymer film that is particularly useful as a phase difference film is obtained.

Besides the above, as the method for obtaining an alignment pattern, it is possible to employ a method that uses no photo-alignment film, such as a method for rubbing an alignment film with a probe of an AFM (atomic force microscope) or a method for etching an optically anisotropic body. However, a method that uses a photo-alignment film is simple and thus preferable.

Examples of the method for applying the polymerizable liquid crystal composition of the present invention to the support include known and conventional coating methods such as bar coating, spin coating, roll coating, gravure coating, spraying coating, die coating, cap coating, and dipping. When employing such a method, to increase coatability, a known and conventional organic solvent can be added to the polymerizable liquid crystal composition of the present invention. In this case, it is possible to remove the organic solvent by natural drying, heat-drying, drying under reduced pressure, heat-drying under reduced pressure, etc., after the polymerizable liquid crystal composition of the present invention is applied to the support.

It is preferable that after the application of the composition, the liquid crystal compound in the polymerizable liquid crystal composition of the present invention is uniformly aligned in the state of retaining a cholesteric phase. In particular, the alignment can be facilitated further by performing a heating treatment that facilitates alignment of liquid crystal. The temperature of the heating treatment is generally 50 to 150° C., preferably 70 to 140° C. The time of the heating treatment is generally 0.5 to 15 minutes, preferably 2 to 10 minutes.

A desirable heat treatment method is as follows. For example, the polymerizable liquid crystal composition of the present invention is applied to the support and then heated to the C(solid phase)-N(nematic phase) transition temperature (hereinafter referred to as "C—N transition temperature") or higher of the liquid crystal composition to make the polymerizable liquid crystal composition be in a liquid crystal state or in an isotropic phase liquid state. Then, if necessary, the composition is gradually cooled to exhibit a cholesteric phase. At this stage, the composition is kept at a temperature that allows the composition to be in a liquid crystal phase, so that a liquid crystal phase domain is sufficiently developed to be a monodomain.

It is also possible that after the polymerizable liquid crystal composition of the present invention is applied to the support, a heating treatment can be performed thereon, which keeps the temperature of the composition within the temperature range that allows the composition to exhibit a cholesteric phase for a predetermined period of time. The heating treatment time is not particularly limited; however, it is generally 1 to 60 minutes, preferably 2 to 30 minutes.

When the heating temperature is too high, the polymerizable liquid crystal compound can cause an undesirable polymerization reaction and thus deteriorate. When the polymerizable liquid crystal composition is cooled too much, it can cause phase separation and thus exhibit precipitation of crystals or a higher liquid crystal phase such as a smectic phase; therefore, it can be impossible to perform the alignment treatment.

A liquid crystal polymer film can be produced by performing such a heating treatment, which has less alignment defects and uniform alignment compared to a coating method which consists of simply a coating step.

It is also possible to obtain a liquid crystal polymer film by, after performing the uniform alignment treatment as described above, cooling the polymerizable liquid crystal composition the lowest temperature at which the liquid crystal phase causes no phase separation, that is, into a supercooled state, and then polymerizing the composition at the same temperature in the state that the liquid crystal phase is aligned. Thereby, a liquid crystal polymer film having a better alignment order and excellent transparency is obtained.

Examples of the method for polymerizing the polymerizable liquid crystal composition include a method for applying active energy rays and a thermal polymerization method. Since no heating is required and the reaction proceeds at room temperature, the method for applying active energy rays is preferred. Due to simple operation, a method for applying light such as ultraviolet light is particularly preferable.

Upon the exposure, the temperature is set to a temperature at which the polymerizable liquid crystal composition can retain the liquid crystal phase and, if at all possible, the temperature is preferably set to 30° C. or less to prevent the polymerizable liquid crystal compound or the polymerizable liquid crystal composition from inducing thermal polymerization. In the temperature increasing process, generally the polymerizable liquid crystal compound and the polymerizable liquid crystal composition exhibit a liquid crystal phase within the range from the C—N transition temperature to the N (nematic phase)-I (isotropic liquid phase) transition temperature (hereinafter referred to as "N-I transition temperature"). On the other hand, in the temperature decreasing process, the polymerizable liquid crystal compound and the polymerizable liquid crystal composition keep a thermodynamically non-equilibrium state, so that sometimes they are not solidified even at the C—N transition temperature or less and keep a liquid crystal state. This state is called a supercooled state. In the present invention, the polymerizable liquid crystal compound and polymerizable liquid crystal composition in the supercooled state are considered to be in the state of retaining a liquid crystal phase. Ultraviolet irradiation intensity is generally in the range of 1 W/m² to 10 kW/m², preferably in the range of 5 W/m² to 2 kW/m².

A liquid crystal polymer film having regions in different alignment directions can be obtained by, after a specific region only is polymerized by exposure to ultraviolet light through a mask, changing the alignment state of a non-polymerized region by applying an electric or magnetic field or by heating, and then polymerizing the non-polymerized region.

A liquid crystal polymer film having regions in different alignment directions can be also obtained by, before a specific region only is polymerized by exposure to ultraviolet light through a mask, previously controlling the alignment of the polymerizable liquid crystal composition which is in an unpolymerized state by applying an electric or magnetic field or by heating, and then polymerizing the same kept in that state by exposure to light through a mask.

The liquid crystal polymer obtained by (co)polymerization of the polymerizable liquid crystal composition of the present invention can be used solely as an optically anisotropic body after removing the support therefrom, or it can be used as it is as an optically anisotropic body without removing the support.

Particularly, the liquid crystal polymer film obtained by (co)polymerization of the polymerizable liquid crystal composition of the present invention is a cholesteric liquid crystal film and has a significantly high reflectance, so that it is suitable as a polarizer of a liquid crystal display element.

Also, it is possible to obtain a multilayered polarizer that corresponds to all lights in the visible region of a spectrum by laminating a plurality of such a liquid crystal polymer film using a laminating method and appropriately selecting the wavelength of a liquid crystal polymer film to be selected (see EP No. 0720041).

Instead of such a multilayered polarizer, the liquid crystal polymer film can be used as a broad-band polarizer in combination with an appropriate compound and processing condition. Examples of the method for using such a polarizer include those disclosed in WO98/08135, EP0606940, GB2312529 and WO96/02016.

It is also possible to produce a color filter by using the polymerizable liquid crystal composition of the present invention. A required wavelength can be provided appropriately to the filter by a coating method which is known for one skilled in the art.

Also, it is possible to utilize the thermal discoloration properties of cholesteric liquid crystal. The color of a cholesteric layer is changed from red, green to blue by controlling the temperature. A specific region can be polymerized at a predetermined temperature using a mask.

The liquid crystal polymer of the present invention obtained in the manner as described above uses the left-handed-helix-inducing polymerizable chiral compound of the present invention; therefore, it has left-handed helical (left-twisted) selective reflection property.

Being left-handed helical can be confirmed by selective reflection of left-handed circularly-polarized light in spectrophotometric measurement, for example.

The helical twisting power (HTP) of the liquid crystal polymer of the present invention is preferably 12 or more.

HTP is obtained by the following formula:

$$HTP=1/(P \times C)=n/(\lambda \times C) \qquad \text{[Mathematical Formula 1]}$$

wherein P, C, n and λ refer to the following meanings:

P: Helical pitch length of liquid crystal polymer (μm)

C: Concentration of chiral agent in polymerizable liquid crystal compound (% by mass)

n: Average refractive index of polymerizable liquid crystal compound

λ: Median value of selective reflection range of liquid crystal polymer (μm)

Median wavelength λ can be obtained as a selective reflection value measured by the transmission spectrum of the liquid crystal polymer with a spectrometer.

The liquid crystal polymer of the present invention obtained in the manner as described above generally has a number average molecular weight of 500 to 1,000,000, preferably 500 to 500,000, more preferably 5,000 to 300,000. The number average molecular weight is preferably in the above range because high film hardness and excellent handling properties are obtained. The number average molecular weight of the liquid crystal polymer can be measured by gel permeation chromatography (GPC) using monodispersed polystyrene as a standard sample and tetrahydrofuran (THF) as an eluent.

In the liquid crystal polymer of the present invention, it is presumed that crosslinking points are uniformly present in a molecule thereof. Since the liquid crystal polymer is obtained by (co)polymerizing the polymerizable liquid crystal compound of the present invention, it has high cross-linking efficiency and excellent hardness.

The liquid crystal polymer of the present invention can be used as a constitutional material of an optically anisotropic body by utilizing the anisotropy of its physical properties such as alignment (orientation), refractive index, conductivity and susceptibility. Examples of the constitutional material include a retardation plate, an alignment film for liquid crystal display elements, a polarizing plate, a viewing angle widening plate, a color filter, a low-pass filter, a light polarization prism and various kinds of optical filters.

(4) Optically Anisotropic Body

The fourth invention of the present invention is an optically anisotropic body comprising the liquid crystal polymer of the present invention as a constitutional material.

Examples of the optically anisotropic body of the present invention include a retardation plate, an alignment film for liquid crystal display elements, a polarizing plate, a viewing angle widening plate, a color filter, a low-pass filter, a light polarization prism and various kinds of optical filters.

The optically anisotropic body of the present invention comprises, as a constitutional material, the liquid crystal polymer obtained by polymerizing the polymerizable liquid crystal composition of the present invention; therefore, the optically anisotropic body of the present invention has uniform and high-quality liquid crystal alignment.

EXAMPLES

The present invention will be described further in detail with reference to examples. However, the scope of the present invention may not be limited to the following examples. Herein, "part(s)" and "%" are based on mass unless otherwise noted.

The ratio of a developing solvent (solvent ratio represented in parentheses) used for column chromatography is a volume ratio.

Example 1

Synthesis of Polymerizable Chiral Compound (I-1)

[Chemical Formula 17]

(I-1)

<Step 1>

Intermediate A represented by the following formula was produced:

[Chemical Formula 18]

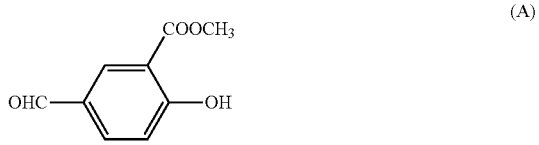

(A)

In a four-neck reactor provided with a condenser, a thermometer and a dropping funnel, under a nitrogen flow, 15 g (0.09 mol) of 5-formylsalicylic acid, 14.5 g (0.45 mol) of methanol and 4-(dimethylamino)pyridine were dissolved in 200 mL of THF. To the thus-obtained solution, at 25° C., 37.3 g (0.18 mol) of N,N-dicyclohexylcarbodiimide dissolved in 100 mL of THF was gradually added with a dropping funnel to react for 6 hours at 25° C. After the reaction, the resultant was filtered under reduced pressure. Then, THF was removed with a rotary evaporator under reduced pressure to obtain yellow oil. This yellow oil was purified by silica gel column chromatography (n-hexane:THF=9:1), thereby obtaining 13.4 g of white solids (intermediate A) (yield: 82.4%). The structure was identified by $^1$H-NMR.

($^1$H-NMR data of intermediate A)

$^1$H-NMR (500 MHz, CDCl$_3$, TMS, δ ppm): 11.36 (s, 1H), 9.88 (s, 1H), 8.39 (s, 1H), 8.00 (d, 1H, J=9.0 Hz), 7.11 (d, 1H, J=9.0 Hz), 4.01 (s, 3H)

<Step 2>

Intermediate B represented by the following formula was produced:

[Chemical Formula 19]

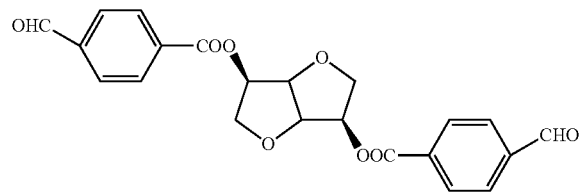

(B)

In a four-neck reactor provided with a thermometer, under a nitrogen flow, 86.3 g (0.57 mol) of terephthalaldehydic acid, 40 g (0.27 mol) of isomannide and 7.0 g (0.057 mol) of 4-(dimethylamino)pyridine were dissolved in 650 mL of N-methylpyrrolidone. To the thus-obtained solution, in a water bath, 110.2 g (0.57 mol) of 1-ethyl-3-(3-dimethylaminopropyl)carbodiimide hydrochloride (WSC) was gradually added to react for 15 hours at 25° C. After the reaction, the reaction solution was mixed with 5 L of water and then extracted twice with 500 mL of ethyl acetate. After a water layer was removed by separation, the thus-obtained ethyl acetate layer was dried over anhydrous magnesium sulfate and then filtered under reduced pressure to remove magnesium sulfate. The ethyl acetate layer was condensed under reduced pressure with a rotary evaporator to obtain light yellow oil. The thus-obtained light yellow oil was purified by silica gel column chromatography (n-hexane:THF=3:2), thereby obtaining 30 g of white solids (intermediate B) (yield: 28.7%). The structure was identified by $^1$H-NMR.

($^1$H-NMR data of intermediate B)

$^1$H-NMR (400 MHz, CDCl$_3$, TMS, δ ppm): 10.10 (s, 2H), 8.24 (d, 4H, J=8.2 Hz), 7.96 (d, 4H, J=8.2 Hz), 5.37 (dd, 2H, J=6.4 Hz, 8.0 Hz), 4.90 (dd, 2H, J=6.4 Hz, 8.0 Hz), 4.45 (dd, 2H, J=6.4 Hz, 9.5 Hz), 4.03 (dd, 2H, J=6.4 Hz, 9.5 Hz)

<Step 3>

Intermediate C represented by the following formula was produced:

[Chemical Formula 20]

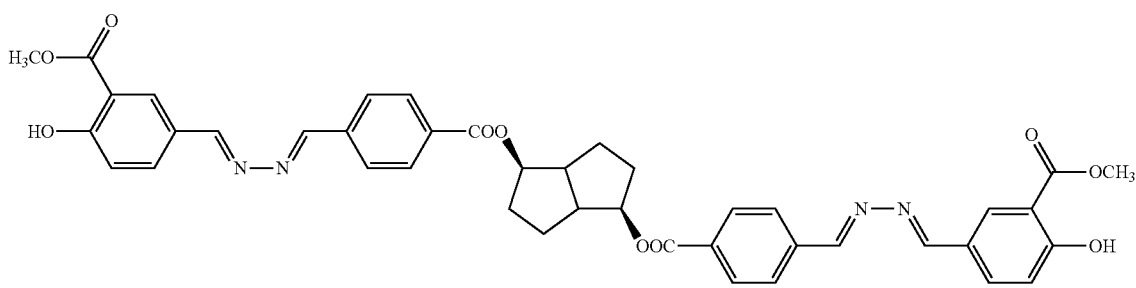

(C)

In a four-neck reactor provided with a thermometer, under a nitrogen flow, 23 g (0.46 mol) of hydrazine monohydrate was dissolved in 100 mL of 2-propanol. To the thus-obtained solution, a solution obtained by dissolving 8.2 g (0.046 mol) of intermediate A in 50 mL of THF, was gradually added at 25° C. After the addition, the resultant was stirred at 25° C. for 10 minutes. Then, the reaction solution was mixed 800 mL of saturated sodium bicarbonate water and then extracted twice with 100 mL of chloroform. The thus-extracted chloroform layer was washed with 200 mL of 10% sodium bicarbonate water and dried over anhydrous sodium sulfate. After removing the sodium sulfate from the layer by filtration, the chloroform was removed from the layer under reduced pressure with a rotary evaporator to obtain 4.2 g of light yellow solids. The light yellow solids were dissolved in 50 mL of THF and mixed with 4.5 g (0.011 mol) of intermediate B to react at 25° C. for 12 hours. The thus-precipitated crystals were collected by filtration and washed with THF to obtain 4.1 g of yellow solids containing intermediate C. Since the yellow solids had low solubility in solvents that can be used for purification and they were difficult to purify, the yellow solids containing intermediate C were used in the following step as they are.
<Step 4> Synthesis of Compound (I-1)
In a four-neck reactor provided with a thermometer, under a nitrogen flow, 1.0 g of the yellow solids comprising intermediate C synthesized in the above Step 3, 0.96 g (3.3 mmol) of 4-(6-acryloyl-hex-1-yloxy)benzoic acid (manufactured by DKSH Japan K.K.) and 40 mg (0.33 mmol) of 4-(dimethylamino)pyridine were dissolved in 200 mL of N-methylpyrrolidone. To the thus-obtained solution, 0.76 g (4 mmol) of 1-ethyl-3-(3-dimethylaminopropyl)carbodiimide hydrochloride (WSC) was added at 25° C. to react for 18 hours at 25° C. After the reaction, the reaction solution was mixed with 800 mL of water and then extracted twice with 150 mL of ethyl acetate. An ethyl acetate layer was separated therefrom, dried over anhydrous magnesium sulfate and then filtered to remove magnesium sulfate. The ethyl acetate layer was condensed under reduced pressure with a rotary evaporator to obtain yellow oil. The thus-obtained yellow oil was purified by silica gel column chromatography (toluene:ethyl acetate=8:2), thereby obtaining 0.75 g of compound (I-1) in the form of light yellow solids. The structure was identified by $^1$H-NMR.

($^1$H-NMR data of compound (I-1))
$^1$H-NMR (400 MHz, CDCl$_3$, TMS, δ ppm): 8.70 (s, 2H), 8.70 (s, 2H), 8.49 (d, 2H, J=2.3 Hz), 8.19-8.10 (m, 10H), 7.94 (d, 4H, J=8.7 Hz), 7.34 (d, 2H, J=8.2 Hz), 6.98 (d, 4H, J=8.7 Hz), 6.40 (dd, 2H, J=1.4 Hz, 17.4 Hz), 6.13 (dd, 2H, J=10.5 Hz, 17.4 Hz), 5.82 (dd, 2H, J=1.4 Hz, 10.5 Hz), 5.40-5.35 (m, 2H), 4.93-4.90 (m, 2H), 4.19-4.15 (m, 6H), 4.08-4.03 (m, 6H), 3.78 (s, 6H), 1.87-1.81 (m, 4H), 1.76-1.69 (m, 4H), 1.57-1.42 (m, 8H)

Example 2

Synthesis of Polymerizable Chiral Compound (I-2)

[Chemical Formula 21]

<Step 1>
Intermediate D represented by the following formula was produced:

[Chemical Formual 22]

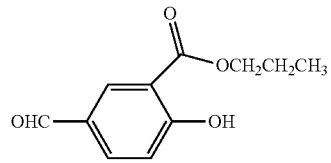

(D)

In a four-neck reactor provided with a condenser, a thermometer and a dropping funnel, under a nitrogen flow, 15 g (0.09 mol) of 5-formylsalicylic acid, 27.1 g (0.45 mol) of 1-propanol and 4-(dimethylamino)pyridine were dissolved in 200 mL of THF. To the thus-obtained solution, at 25° C., 26.0 g (0.14 mol) of 1-ethyl-3-(3-dimethylaminopropyl)carbodiimide hydrochloride (WSC) dissolved in 100 mL of THF was gradually added to react for 16 hours at 25° C. After the reaction, the reaction solution was mixed with 2 L of water and then extracted twice with 500 mL of ethyl acetate. An ethyl acetate layer was separated therefrom, dried over anhydrous magnesium sulfate and then filtered under reduced pressure to remove magnesium sulfate. The ethyl acetate layer was condensed under reduced pressure with a rotary evaporator to obtain yellow oil. The thus-obtained yellow oil was purified by silica gel column chromatography (n-hexane:ethylacetate=85:15), thereby obtaining 15.0 g of white solids (intermediate D) (yield: 80.0%). The structure was identified by $^1$H-NMR.

($^1$H-NMR data of intermediate D)
$^1$H-NMR (400 MHz, CDCl$_3$, TMS, δ ppm): 11.48 (s, 1H), 9.88 (s, 1H), 8.37 (s, 1H), 7.99 (d, 1H, J=8.4 Hz), 7.09 (d, 1H, J=8.4 Hz), 4.35 (t, 2H, J=6.9 Hz), 1.84 (tq, 2H, J=6.9 Hz, 7.3 Hz), 1.05 (t, 3H, J=7.3 Hz)

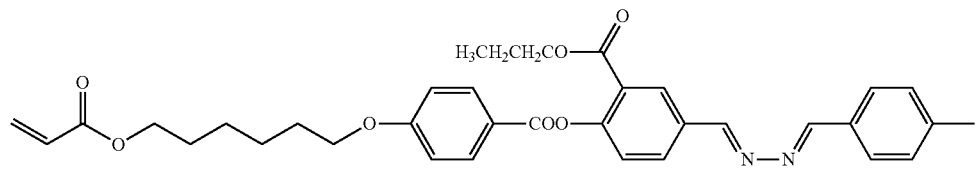

(I-2)

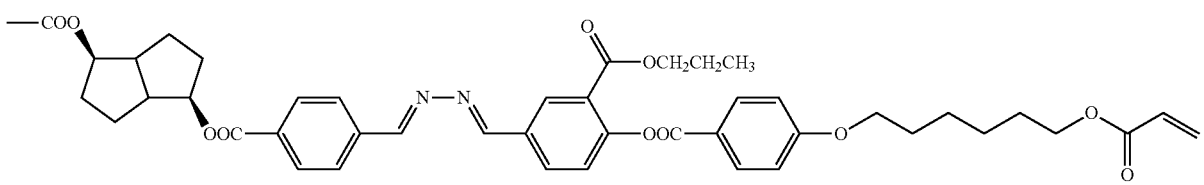

<Step 2>
Intermediate E represented by the following formula was produced:

[Chemical Formula 23]

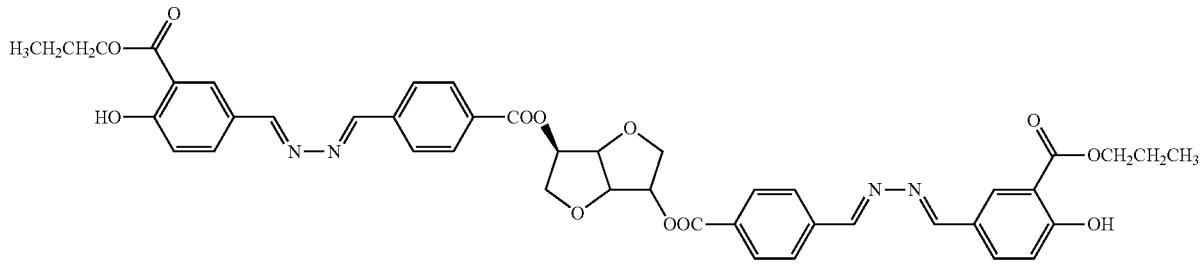

(E)

In a four-neck reactor provided with a thermometer, under a nitrogen flow, 5.4 g (0.11 mol) of hydrazine monohydrate was dissolved in 40 mL of 2-propanol. To the thus-obtained solution, a solution obtained by dissolving 4.5 g (0.034 mol) of intermediate D in 30 mL of THF was gradually added in a dropwise manner at 25° C. After stirring the solution at 25° C. for 30 minutes, the solution was mixed with 100 mL of saturated sodium bicarbonate water and then extracted twice with 50 mL of chloroform. A chloroform layer was removed there from by separation, washed with 50 mL of 10% sodium bicarbonate water and then dried over anhydrous sodium sulfate. After removing sodium sulfate from the layer by filtration, the chloroform was removed from the layer under reduced pressure with a rotary evaporator to obtain 4.1 g of light yellow solids. The light yellow solids were dissolved in 50 mL of THF and mixed with 3.9 g (0.0092 mol) of intermediate B to react at 25° C. for 11 hours. The thus-precipitated crystals were collected by filtration and washed with THF to obtain 3.6 g of yellow solids containing intermediate E. Since the yellow solids had low solubility in solvents that can be used for purification and they were difficult to purify, the yellow solids containing intermediate E were used in the following step as they are.

<Step 3> Synthesis of Compound (I-2)

In a four-neck reactor provided with a thermometer, under a nitrogen flow, 2.0 g (2.5 mmol) of the yellow solids comprising intermediate E synthesized in the above Step 3, 1.8 g (6.2 mmol) of 4-(6-acryloyl-hex-1-yloxy)benzoic acid (manufactured by DKSH Japan K.K.) and 91 mg (0.75 mmol) of 4-(dimethylamino)pyridine were dissolved in 130 mL of N-methylpyrrolidone. To the thus-obtained solution, 1.4 g (7.5 mmol) of 1-ethyl-3-(3-dimethylaminopropyl)carbodiimide hydrochloride (WSC) was added at 25° C. to react for 24 hours at 25° C. After the reaction, the reaction solution was mixed with 1 L of water and then extracted twice with 200 mL of ethyl acetate. The resulting ethyl acetate layer was dried over anhydrous magnesium sulfate and then filtered to remove magnesium sulfate. The ethyl acetate layer was condensed under reduced pressure with a rotary evaporator to obtain yellow oil. The thus-obtained yellow oil was purified by silica gel column chromatography (toluene:ethyl acetate=9:1), thereby obtaining 0.65 g of compound (I-2) in the form of light yellow solids. The structure was identified by $^1$H-NMR.

($^1$H-NMR data of compound (I-2))

$^1$H-NMR (400 MHz, CDCl$_3$, TMS, δ ppm): 8.70 (s, 4H), 8.47 (d, 2H, J=1.4 Hz), 8.19-8.11 (m, 10H), 7.94 (d, 4H, J=8.2 Hz), 7.32 (d, 2H, J=8.7 Hz), 6.97 (d, 4H, J=8.7 Hz), 6.40 (dd, 2H, J=1.4 Hz, 17.2 Hz), 6.12 (dd, 2H, J=10.6 Hz, 17.2 Hz), 5.82 (dd, 2H, J=1.4 Hz, 10.6 Hz), 5.37 (d, 2H, J=4.6 Hz), 4.92 (d, 2H, J=4.6 Hz), 4.18-4.05 (m, 16H), 1.87-1.81 (m, 4H), 1.76-1.69 (m, 4H), 1.60-1.46 (m, 12H), 0.86 (t, 6H, J=7.3 Hz)

Example 3

Synthesis of Polymerizable Chiral Compound (I-3)

[Chemical Formula 24]

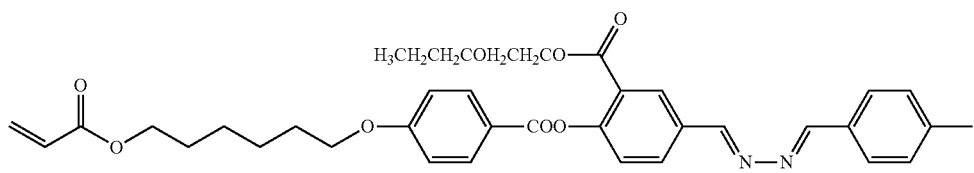

(I-3)

-continued

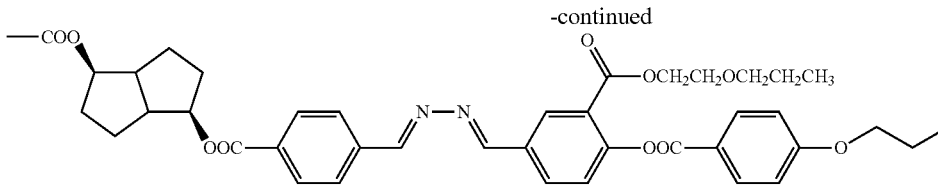

<Step 1>
Intermediate F represented by the following formula was produced:

[Chemical Formula 25]

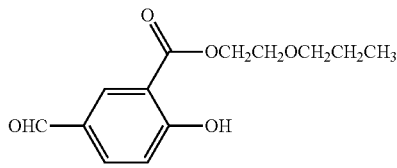

In a four-neck reactor provided with a condenser, a thermometer and a dropping funnel, under a nitrogen flow, 5 g (0.03 mol) of 5-formylsalicylic acid, 15.6 g (0.15 mol) of ethylene glycol monopropyl ether and 0.48 g (4 mmol) of 4-(dimethylamino)pyridine were dissolved in 200 mL of N-methylpyrrolidone. To the thus-obtained solution, 7.6 g (0.04 mol) of 1-ethyl-3-(3-dimethylaminopropyl)carbodiimide hydrochloride (WSC) was added at 25° C. to react for 17 hours at 25° C. After the reaction, the reaction solution was mixed with 800 mL of water and then extracted twice with 200 mL of ethyl acetate. An ethyl acetate layer was separated therefrom, dried over anhydrous magnesium sulfate and then filtered to remove magnesium sulfate. The ethyl acetate layer was condensed with a rotary evaporator to obtain yellow oil. The thus-obtained yellow oil was purified by silica gel column chromatography (toluene:ethyl acetate=8:2), thereby obtaining 6.1 g of white solids (intermediate F) (yield: 80.6%). The structure was identified by $^1$H-NMR.

($^1$H-NMR data of intermediate F)
$^1$H-NMR (400 MHz, CDCl$_3$, TMS, δ ppm): 11.31 (s, 1H), 9.87 (s, 1H), 8.40 (s, 1H), 7.99 (dd, 1H, J=1.6 Hz, 8.8 Hz), 7.09 (d, 1H, J=8.8 Hz), 4.55-4.52 (m, 2H), 3.79-3.75 (m, 2H), 3.47 (t, 2H, J=6.8 Hz), 1.66-1.57 (m, 2H), 0.92 (t, 3H, J=7.3 Hz)

<Step 2>
Intermediate G represented by the following formula was produced:

In a four-neck reactor provided with a thermometer, under a nitrogen flow, 1 g (20 mmol) of hydrazine monohydrate was dissolved in 20 mL of 2-propanol. To the thus-obtained solution, a solution obtained by dissolving 1 g (4 mmol) of intermediate F in 30 mL of THF was gradually added in a dropwise manner at 25° C. After the addition, the solution was stirred at 25° C. for 5 minutes, mixed with 500 mL of saturated sodium bicarbonate water and then extracted twice with 50 mL of chloroform. A chloroform layer was removed therefrom by separation, washed with 100 mL of 10% sodium bicarbonate water and then dried over anhydrous sodium sulfate. After removing sodium sulfate from the layer by filtration, the chloroform was removed from the layer under reduced pressure with a rotary evaporator to obtain 1.1 g of yellow oil. The yellow oil was dissolved in 30 mL of THF, mixed with 0.3 g (0.7 mmol) of intermediate B to react at 25° C. for 17 hours. The thus-precipitated crystals were collected by filtration and washed with THF cooled in an ice bath to obtain 0.3 g of yellow solids containing intermediate G. Since the yellow solids had low solubility in solvents that can be used for purification and they were difficult to purify, the yellow solids containing intermediate G were used in the following step as they are.

<Step 3> Synthesis of Compound (I-3)
In a four-neck reactor provided with a thermometer, under a nitrogen flow, 0.21 g of the yellow solids comprising intermediate G synthesized in the above Step 2, 0.17 g (0.58 mmol) of 4-(6-acryloyl-hex-1-yloxy)benzoic acid (manufactured by DKSH Japan K.K.) and 7 mg (0.06 mmol) of 4-(dimethylamino)pyridine were dissolved in 50 mL of N-methylpyrrolidone. To the thus-obtained solution, 133 mg (0.69 mmol) of 1-ethyl-3-(3-dimethylaminopropyl)carbodiimide hydrochloride (WSC) was added at 25° C. to react for 18 hours at 25° C. After the reaction, the reaction solution was mixed with 300 mL of water and then extracted twice with 100 mL of ethyl acetate. An ethyl acetate layer was separated therefrom, and the obtained ethyl acetate layer was dried over anhydrous magnesium sulfate and then filtered to remove magnesium sulfate. The ethyl acetate layer was condensed with a rotary evaporator to obtain yellow oil. The thus-obtained yellow oil was purified by silica gel column chroma-

[Chemical Formula 26]

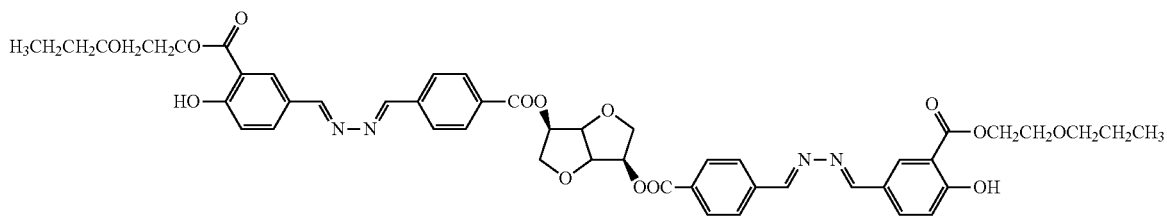

tography (toluene:ethyl acetate=8:2), thereby obtaining 0.15 g of compound (I-3) in the form of light yellow solids. The structure was identified by $^1$H-NMR.

($^1$H-NMR data of compound (I-3))

$^1$H-NMR (400 MHz, CDCl$_3$, TMS, δ ppm): 8.70 (s, 4H), 8.49 (d, 2H, J=2.3 Hz), 8.19-8.12 (m, 10H), 7.94 (d, 4H, J=8.2 Hz), 7.33 (d, 2H, J=8.2 Hz), 6.99-6.96 (m, 4H), 6.40 (dd, 2H, J=1.4 Hz, 17.4 Hz), 6.12 (dd, 2H, J=10.6 Hz, 17.4 Hz), 5.82 (dd, 2H, J=1.4 Hz, 10.6 Hz), 5.40-5.35 (m, 2H), 4.93-4.91 (m, 2H), 4.36-4.33 (m, 4H), 4.19-4.15 (m, 6H), 4.08-4.03 (m, 6H), 3.54-3.52 (m, 4H), 3.31-3.27 (m, 4H), 1.87-1.81 (m, 4H), 1.76-1.69 (m, 4H), 1.56-1.43 (m, 12H), 0.88 (t, 6H, J=7.3 Hz)

Example 4

Synthesis of Polymerizable Chiral Compound (I-4)

[Chemical Formula 27]

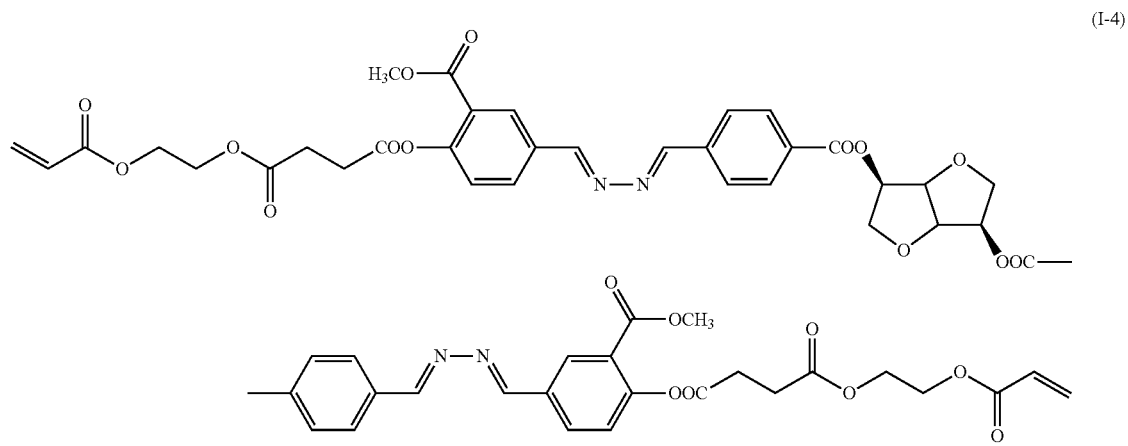

(I-4)

Reaction and post-treatment was performed in the same manner as the compound (I-1) synthesis method, except that 0.71 g (3.3 mmol) of 2-acryloyloxyethylsuccinic acid (manufactured by Kyoeisha Chemical Co., Ltd.) was used in place of 0.96 g of 4-(6-acryloyl-hex-1-yloxy)benzoic acid (manufactured by DKSH Japan K.K.) in compound (I-1) synthesis step 4. The thus-obtained reactant was purified by silica gel column chromatography (toluene:ethyl acetate=9:1), thereby obtaining compound (I-4). The structure was identified by $^1$H-NMR.

($^1$H-NMR data of compound (I-4))

$^1$H-NMR (400 MHz, CDCl$_3$, TMS, δ ppm): 8.69 (s, 2H), 8.66 (s, 2H), 8.46 (d, 2H, J=2.3 Hz), 8.18 (d, 4H, J=8.7 Hz), 8.06 (dd, 2H, J=2.3 Hz, 8.7 Hz), 7.93 (d, 4H, J=8.7 Hz), 7.22 (d, 2H, J=8.7 Hz), 6.43 (dd, 2H, J=1.4 Hz, 17.4 Hz), 6.12 (dd, 2H, J=10.6 Hz, 17.4 Hz), 5.85 (dd, 2H, J=1.4 Hz, 10.6 Hz), 5.39-5.35 (m, 2H), 4.93-4.90 (m, 2H), 4.38 (s, 8H), 4.18-4.14 (m, 2H), 4.07-4.03 (m, 2H), 3.90 (s, 6H), 3.00 (t, 4H, J=6.9 Hz), 2.81 (t, 4H, J=6.9 Hz)

Example 5

Synthesis of Polymerizable Chiral Compound (I-5)

[Chemical Formula 28]

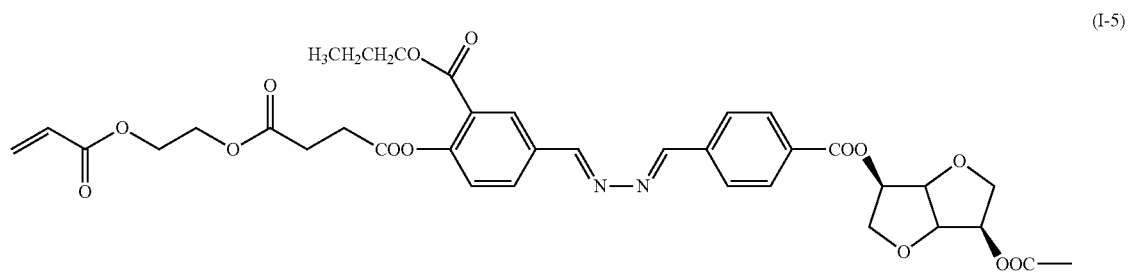

(I-5)

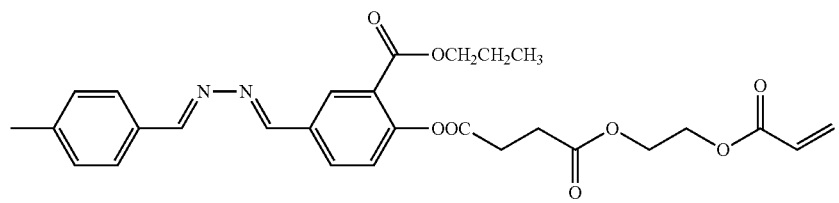

Reaction and post-treatment was performed in the same manner as the compound (I-2) synthesis method, except that 1.4 g (6.5 mmol) of 2-acryloyloxyethylsuccinic acid (manufactured by Kyoeisha Chemical Co., Ltd.) was used in place of 1.8 g of 4-(6-acryloyl-hex-1-yloxy)benzoic acid (manufactured by DKSH Japan K.K.) in compound (I-2) synthesis step 3. The thus-obtained reactant was purified by silica gel column chromatography (toluene:ethyl acetate=9:1), thereby obtaining compound (I-5). The structure was identified by $^1$H-NMR.

($^1$H-NMR data of compound (I-5))

$^1$H-NMR (400 MHz, CDCl$_3$, TMS, δ ppm): 8.69 (s, 2H), 8.67 (s, 2H), 8.43 (d, 2H, J=2.0 Hz), 8.18 (d, 4H, J=8.3 Hz), 8.07 (dd, 2H, J=2.0 Hz, 8.3 Hz), 7.93 (d, 4H, J=8.3 Hz), 7.22 (d, 2H, J=8.3 Hz), 6.43 (dd, 2H, J=0.9 Hz, 17.4 Hz), 6.12 (dd, 2H, J=10.6 Hz, 17.4 Hz), 5.85 (dd, 2H, J=0.9 Hz, 10.6 Hz), 5.39-5.35 (m, 2H), 4.93-4.90 (m, 2H), 4.37 (s, 8H), 4.26 (t, 4H, J=6.8 Hz), 4.18-4.03 (m, 4H), 2.99 (t, 4H, J=6.9 Hz), 2.81 (t, 4H, J=6.9 Hz), 1.79 (tq, 4H, J=6.8 Hz, 7.3 Hz), 1.02 (t, 6H, J=7.3 Hz)

Example 6

Synthesis of Polymerizable Chiral Compound (I-6)

[Chemical Formula 29]

(I-6)

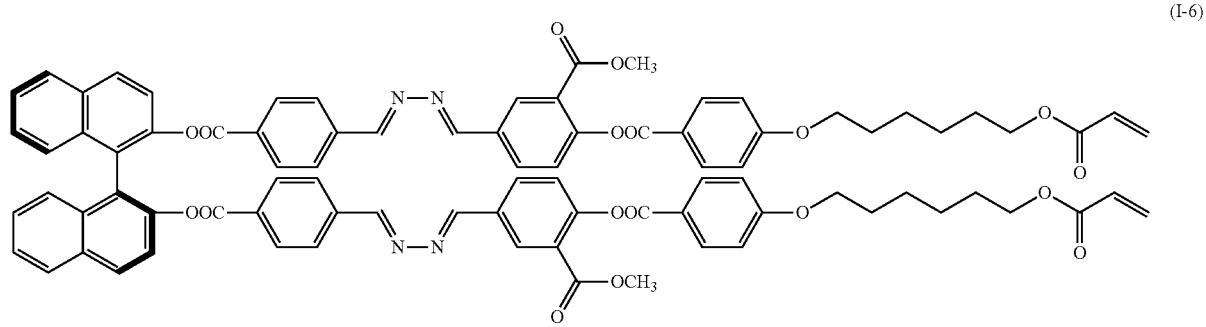

<Step 1>

Intermediate H represented by the following formula was produced:

[Chemical Formula 30]

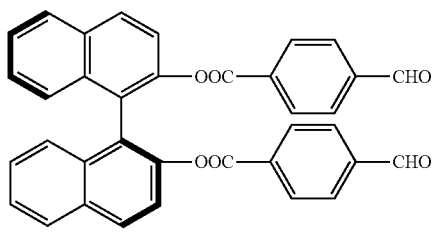

(H)

In a four-neck reactor provided with a thermometer, under a nitrogen flow, 6.6 g (43.7 mmol) of terephthalaldehydic acid, 5 g (17.5 mmol) of (S)-(−)-1,1'-bi-2-naphthol and 0.64 g (5.2 mmol) of 4-(dimethylamino)pyridine were dissolved in 100 mL of N-methylpyrrolidone. To the thus-obtained solution, in a water bath, 10 g (52.4 mmol) of 1-ethyl-3-(3-dimethylaminopropyl)carbodiimide hydrochloride (WSC) was gradually added to react for 20 hours at 25° C. After the reaction, the reaction solution was mixed with 1 L of water and then extracted twice with 300 mL of ethyl acetate. The resulting ethyl acetate layer was dried over anhydrous sodium sulfate and then filtered under reduced pressure to remove sodium sulfate. The ethyl acetate layer was condensed by removing ethyl acetate therefrom under reduced pressure with a rotary evaporator to obtain light yellow oil. The thus-obtained light yellow oil was purified by silica gel column chromatography (toluene:ethyl acetate=95:5), thereby obtaining 2.7 g of light yellow oil (intermediate H) (yield: 28.3%). The structure was identified by $^1$H-NMR.

($^1$H-NMR data of intermediate H)
$^1$H-NMR (500 MHz, CDCl$_3$, TMS, δ ppm): 10.00 (s, 2H), 8.01 (d, 2H, J=9.0 Hz), 7.93 (d, 2H, J=8.0 Hz), 7.77-7.70 (m, 8H), 7.56 (d, 2H, J=8.5 Hz), 7.51-7.47 (m, 2H), 7.43-7.36 (m, 4H)

<Step 2>

Intermediate J represented by the following formula was produced:

[Chemical Formula 31]

(J)

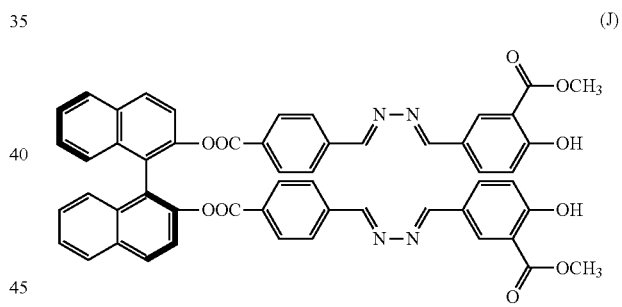

In a four-neck reactor provided with a thermometer, under a nitrogen flow, 2.8 g (55.5 mmol) of hydrazine monohydrate was dissolved in 40 mL of 2-propanol. To the thus-obtained solution, 2 g (11.1 mmol) of intermediate A dissolved in 30 mL of THF was gradually added in a dropwise manner at 25° C. After stirring at 25° C. for 30 minutes, the solution was mixed with 150 mL of saturated sodium bicarbonate water and then extracted twice with 50 mL of chloroform. The thus-extracted chloroform layer was washed with 50 mL of 10% sodium bicarbonate water and then dried over anhydrous sodium sulfate. After removing sodium sulfate from the layer by filtration, the chloroform was removed from the layer under reduced pressure with a rotary evaporator to obtain 1.5 g of light yellow solids. The light yellow solids were dissolved in 50 mL of THF and mixed with 1.7 g (3.1 mmol) of intermediate H to react at 25° C. for 20 hours. After the reaction, the resultant was condensed by removing THF therefrom under reduced pressure with a rotary evaporator to obtain yellow oil. The yellow oil was purified by silica gel column chromatography (toluene:ethyl acetate=95:5), thereby obtaining 0.5 g of yellow solids (intermediate J) (yield: 17.9%). The structure was identified by $^1$H-NMR.

($^1$H-NMR data of intermediate J)

$^1$H-NMR (500 MHz, CDCl$_3$, TMS, δ ppm): 11.13 (s, 2H), 8.57 (s, 2H), 8.56 (s, 2H), 8.26 (d, 2H, J=2.0 Hz), 8.01-7.99 (m, 4H), 7.92 (d, 2H, J=8.0 Hz), 7.71-7.67 (m, 8H), 7.58 (d, 2H, J=9.0 Hz), 7.48-7.41 (m, 4H), 7.37-7.34 (m, 2H), 7.06 (d, 2H, J=8.5 Hz), 3.99 (s, 6H)

<Step 3> Synthesis of Compound (I-6)

In a four-neck reactor provided with a thermometer, under a nitrogen flow, 0.36 g (0.4 mmol) of intermediate J synthesized in the above Step 2, 0.29 g (1 mmol) of 4-(6-acryloylhex-1-yloxy)benzoic acid (manufactured by DKSH Japan K.K.) and 15 mg (0.12 mmol) of 4-(dimethylamino)pyridine were dissolved in 30 mL of N-methylpyrrolidone. To the thus-obtained solution, 230 mg (1.2 mmol) of 1-ethyl-3-(3-dimethylaminopropyl)carbodiimide hydrochloride (WSC) was added at 25° C. to react for 18 hours at 25° C. After the reaction, the reaction solution was mixed with 150 mL of water and then extracted twice with 50 mL of ethyl acetate. The thus-extracted ethyl acetate layer was dried over anhydrous sodium sulfate and then filtered to remove sodium sulfate. The ethyl acetate layer was condensed under reduced pressure with a rotary evaporator to obtain yellow oil. The thus-obtained yellow oil was purified by silica gel column chromatography (toluene:ethyl acetate=9:1), thereby obtaining 0.2 g of compound (I-6) in the form of yellow solids (Yield: 34.4%). The structure was identified by $^1$H-NMR.

($^1$H-NMR data of compound (I-6))

$^1$H-NMR (500 MHz, CDCl$_3$, TMS, δ ppm): 8.65 (s, 2H), 8.59 (s, 2H), 8.48 (d, 2H, J=2.0 Hz), 8.18-8.16 (m, 4H), 8.09 (dd, 2H, J=2.0 Hz, 8.5 Hz), 8.01 (d, 2H, J=9.0 Hz), 7.93 (d, 2H, J=8.5 Hz), 7.74-7.68 (m, 8H), 7.59 (d, 2H, J=9.0 Hz), 7.48-7.42 (m, 4H), 7.38-7.33 (m, 4H), 6.99 (d, 4H, J=9.0 Hz), 6.41 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.19 (t, 4H, J=7.0 Hz), 4.05 (t, 4H, J=6.5 Hz), 3.78 (s, 6H), 1.87-1.82 (m, 4H), 1.76-1.70 (m, 4H), 1.57-1.45 (m, 8H)

Examples 7 to 12 and Reference Example 1

Production of Cured Polymer Film

Corona discharge treatment was performed on both surfaces of a film comprising an alicyclic olefin polymer (Zeonor film ZF16-100 manufactured by Optes Inc.) To one surface thereof, a 5% by mass aqueous solution of polyvinyl alcohol was applied with a #2 wire bar. The thus-obtained coating film was dried at 100° C. for 3 minutes to form a 0.1 μm-thick orientation film. Then, rubbing treatment was performed on the orientation film, thereby obtaining transparent resin substrate 1 having the orientation film.

Next, each of polymerizable chiral compounds (I-1) to (I-6) obtained in Examples 1 to 6 and a polymerizable chiral compound represented by the following formula CD (Paliocolor LC-756 manufactured by BASF):

[Chemical Formula 32]

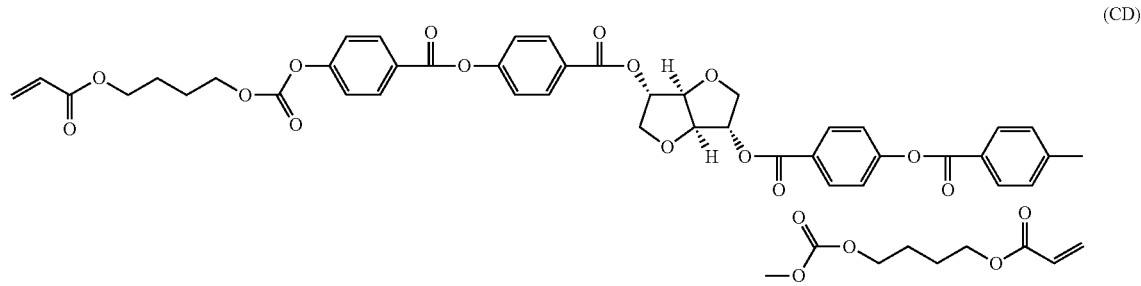

(CD)

a polymerizable liquid crystal compound represented by the following formula LC disclosed under "Examples" of Japanese Patent Application Laid-Open No. 2008-291218:

[Chemical Formula 33]

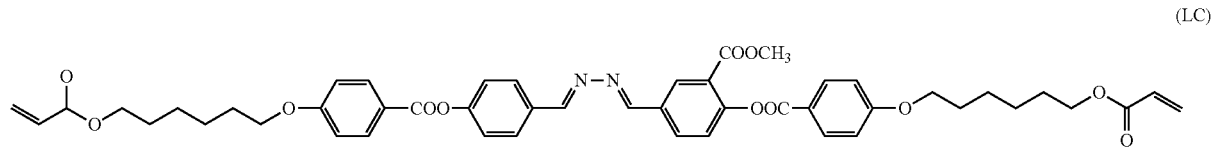

(LC)

a polymerizable non-liquid crystal compound represented by the following formula:

[Chemical Formula 34]

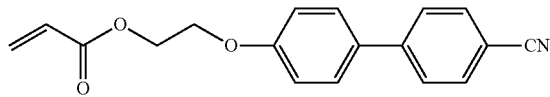

cyclopentanone and 1,3-dioxolan as organic solvents, a surfactant (KH-40 manufactured by AGC Seimi Chemical Co., Ltd.) and a photopolymerization initiator (Irgacure 907 manufactured by Ciba Specialty Chemicals, Inc.) were mixed at the compounding ratio (part(s) by mass) shown in the following table 1 to prepare a cholesteric liquid crystal composition having a solid content of about 40% by mass.

The thus-obtained cholesteric liquid crystal composition was applied to the orientation film-side surface of transparent resin substrate 1 with a #10 wire bar. On the thus-obtained coating film, orientation treatment was performed at 130° C. for 2 minutes to form a cholesteric liquid crystal layer having a dry film thickness of 5 µm. The thus-obtained coating film was irradiated with ultraviolet light at about 2,000 mJ/cm² using a mercury lamp, thereby obtaining a cholesteric cured polymer film having a thickness of about 5 µm, that is, cholesteric cured polymer films 1 to 6 and 1r.

wherein P, C, n and λ refer to the following meanings:

P: Helical pitch length of cholesteric cured polymer film (µm)

C: Concentration of chiral agent in polymerizable liquid crystal compound (% by mass)

n: Average refractive index of polymerizable liquid crystal compound

λ: Median value of selective reflection range of cholesteric cured polymer film (µm)

Median wavelength λ was obtained as a selective reflection value measured by the transmission spectrum of the cholesteric cured polymer film with a spectrometer (Multi Channel Photo Detector MCPD-3000 manufactured by Otsuka Electronics Co., Ltd.) The results are shown in the following Table 2.

When measuring the transmission spectrum, moreover, right- and left-handed circularly-polarized lights were each used as incident light to check the presence of selective reflection of each light. As for helical direction, one which selectively reflects right-handed circularly polarized light is right-handed helical, while one which selectively reflects left-handed circularly polarized light is left-handed helical. The results are shown in Table 2, in which one that showed selective reflection is represented by "o", and one that showed no selective reflection is represented by "x".

TABLE 1

| | Cured polymer layer | Polymerizable liquid crystal compound (part(s) by mass) | Polymerizable non-liquid crystal compound (part(s) by mass) | Polymerizable chiral compound Type | Part(s) by mass | Cyclopentanone (part(s) by mass) | 1,3-dioxolan (part(s) by mass) | Surfactant (part(s) by mass) | Photopolymerization initiator (part(s) by mass) |
|---|---|---|---|---|---|---|---|---|---|
| Example 7 | 1 | 28.4 | 7.0 | Compound (I-1) | 4.6 | 36 | 24 | 0.04 | 12 |
| Example 8 | 2 | 28.4 | 7.0 | Compound (I-2) | 4.6 | 36 | 24 | 0.04 | 12 |
| Example 9 | 3 | 28.4 | 7.0 | Compound (I-3) | 4.6 | 36 | 24 | 0.04 | 12 |
| Example 10 | 4 | 27.7 | 6.9 | Compound (I-4) | 5.4 | 36 | 24 | 0.04 | 12 |
| Example 11 | 5 | 26.4 | 6.6 | Compound (I-5) | 7.0 | 36 | 24 | 0.04 | 12 |
| Example 12 | 6 | 30.1 | 7.6 | Compound (I-6) | 2.3 | 36 | 24 | 0.04 | 12 |
| Reference Example 1 | 1r | 30.0 | 7.5 | CD | 2.4 | 36 | 24 | 0.04 | 12 |

The helical twisting power (HTP) of the obtained cholesteric cured polymer films 1 to 6 and 1r were calculated by the following formula:

$$HTP = 1/(P \times C) = n/(\lambda \times C)$$ [Mathematical Formula 2]

TABLE 2

| | | Presence of selective reflection | | | | |
|---|---|---|---|---|---|---|
| | Cured polymer layer | Right-handed circularly polarized light | Left-handed circularly polarized light | Helical direction | Median wavelength (nm) | HTP (µm⁻¹) |
| Example 7 | 1 | x | o | Left-handed helical | 687 | 20.1 |

TABLE 2-continued

| | | Presence of selective reflection | | | | |
|---|---|---|---|---|---|---|
| | Cured polymer layer | Right-handed circularly polarized light | Left-handed circularly polarized light | Helical direction | Median wavelength (nm) | HTP ($\mu m^{-1}$) |
| Example 8 | 2 | x | o | Left-handed helical | 745 | 18.6 |
| Example 9 | 3 | x | o | Left-handed helical | 807 | 17.2 |
| Example 10 | 4 | x | o | Left-handed helical | 750 | 15.8 |
| Example 11 | 5 | x | o | Left-handed helical | 725 | 12.6 |
| Example 12 | 6 | x | o | Left-handed helical | 465 | 61.4 |
| Reference Example 1 | 1r | o | x | Right-handed helical | 550 | 48.5 |

It is clear from Table 2 that the polymerizable chiral compounds (I-1) to (I-6) obtained in Examples 1 to 6 induce left-handed helix and, among the thus-obtained cholesteric cured polymer films, especially Example 12 has high HTP, which comprises compound (X-ii) as a chiral source.

The invention claimed is:

1. A left-handed-helix-inducing polymerizable chiral compound represented by the following formula (I):

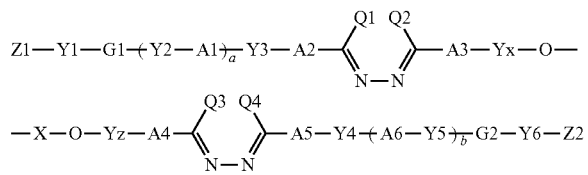

(I)

wherein X represents the following formula (X-i) or (X-ii):

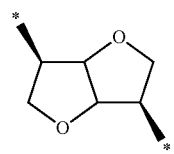

(X-i)

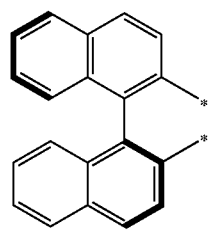

(X-ii)

wherein * represents a bond;
wherein Y1 to Y6 are each independently one selected from the group consisting of a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$— and —NR$^1$—O—, and R$^1$ is a hydrogen atom or an alkyl group having 1 to 6 carbon atoms;
wherein Yx is one selected from the group consisting of a chemical single bond, —C(=O)—, —O—C(=O)—, —NR$^2$—C(=O)—, —CH=CH—C(=O)—, —CH$_2$—, —C$_2$H$_4$— and —CF$_2$—, and R$^2$ is a hydrogen atom or an alkyl group having 1 to 6 carbon atoms;
wherein Yz is one selected from the group consisting of a chemical single bond, —C(=O)—, —C(=O)—O—, —C(=O)—NR$^3$—, —C(=O)—CH=CH—, —CH$_2$—, —C$_2$H$_4$— and —CF$_2$—, and R$^3$ is a hydrogen atom or an alkyl group having 1 to 6 carbon atoms;
wherein G1 and G2 are each independently a divalent aliphatic group which has 1 to 20 carbon atoms and which may have a substituent; the aliphatic group may contain one selected from the group consisting of —O—, —S—, —O—C(=O)—, —C(=O)—O—, —O—C(=O)—O—, —NR$^4$—C(=O)—, —C(=O)—NR$^4$—, —NR$^4$— and —C(=O)—, except the case where two or more adjacent —O— and two or more adjacent —S— are contained in the aliphatic group; and R$^4$ is a hydrogen atom or an alkyl group having 1 to 6 carbon atoms;
wherein Z1 and Z2 are each independently an alkenyl group which has 2 to 10 carbon atoms and which may be substituted by a halogen atom;
wherein Q1 to Q4 are each independently a hydrogen atom or an alkyl group which has 1 to 6 carbon atoms and which may have a substituent;
wherein A1 to A6 are each independently a divalent organic group having 1 to 30 carbon atoms; and
wherein a and b are each independently 0 or 1.

2. The left-handed-helix-inducing polymerizable chiral compound according to claim 1, wherein A1 to A6 of the formula (I) are each independently a phenylene group which may have a substituent, a biphenylene group which may have a substituent, or a naphthylene group which may have a substituent.

3. The left-handed-helix-inducing polymerizable chiral compound according to claim 1, wherein Z1 and Z2 of the formula (I) are each independently one selected from the group consisting of CH$_2$=CH—, CH$_2$=C(CH$_3$)—, CH$_2$=C(Cl)—, CH$_2$=CH—CH$_2$—, CH$_2$=C(CH$_3$)—CH$_2$—, CH$_2$=C(CH$_3$)—CH$_2$CH$_2$—, (CH$_3$)$_2$C=CH—CH$_2$—, CH$_3$—CH=CH— and CH$_3$—CH=CH—CH$_2$—.

4. The left-handed-helix-inducing polymerizable chiral compound according to claim 1, in the formula (I), wherein Y1 to Y6 are each independently —C(═O)—O—, —O—C(═O)— or —O—;
wherein Yx and Yz are each —C(═O)—;
wherein G1 and G2 are each independently —(CH$_2$)$_6$— or —(CH$_2$)$_4$—, in both of which —O—, —C(═O)—O— or —O—C(═O)— may be contained;
wherein Z1 and Z2 are each independently CH$_2$═CH—, CH$_2$═C(CH$_3$)— or CH$_2$═C(Cl)—; and
wherein A1 to A6 are each independently any one of groups represented by the following (A-i), (A-ii) and (A-iii):

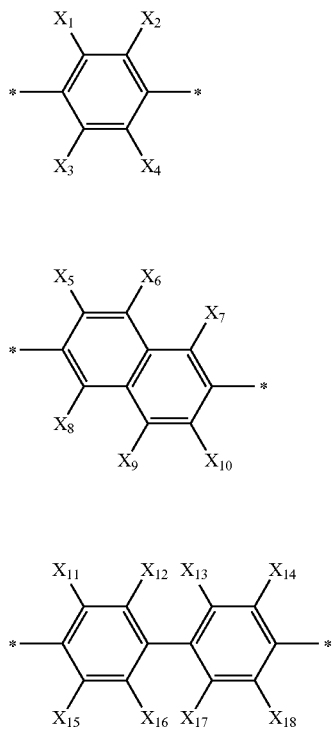

wherein * represents a bond; $X_1$ to $X_{18}$ are each independently one selected from the group consisting of a hydrogen atom, a halogen atom, an alkyl group which has 1 to 10 carbon atoms and which may have a substituent, a cyano group, a nitro group, —OR$^5$, —O—C(═O)—R$^5$, —C(═O)—OR$^5$, —O—C(═O)—OR$^5$, —NR$^6$—C(═O)—R$^5$, —C(═O)—N(R$^5$)R$^6$ and —O—C(═O)—N(R$^5$)R$^6$; R$^5$ and R$^6$ are each independently a hydrogen atom or an alkyl group which has 1 to 10 carbon atoms and which may have a substituent; with the provision that if R$^5$ and/or R$^6$ is an alkyl group, the alkyl group may contain one selected from the group consisting of —O—, —S—, —O—C(═O)—, —C(═O)—O—, —O—C(═O)—O—, —NR$^7$—C(═O)—, —C(═O)—NR$^7$—, —NR$^7$— and —C(═O)—, except the case where two or more adjacent —O— and two or more adjacent —S— are contained in the alkyl group; and R$^7$ is a hydrogen atom or an alkyl group having 1 to 6 carbon atoms.

5. The left-handed-helix-inducing polymerizable chiral compound according to claim 1,
in the formula (I), wherein Y1 to Y6 are each independently —C(═O)—O—, —O—C(═O)— or —O—;
wherein Yx and Yz are each —C(═O)—;
wherein G1 and G2 are each independently —(CH$_2$)$_6$— or —(CH$_2$)$_4$—;
wherein Z1 and Z2 are each independently CH$_2$═CH— or CH$_2$═C(CH$_3$)—; and
wherein A1 to A6 are each independently a group represented by the following (A-i) or (A-ii):

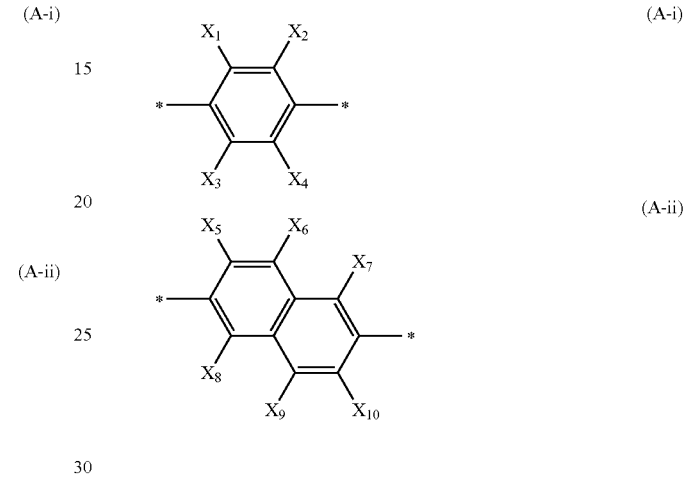

wherein * represents a bond; $X_1$ to $X_{10}$ are each independently one selected from the group consisting of a hydrogen atom, a halogen atom, an alkyl group which has 1 to 10 carbon atoms and which may have a substituent, a cyano group, a nitro group, —OR$^5$, —O—C(═O)—R$^5$, —C(═O)—OR$^5$, —O—C(═O)—OR$^5$, —NR$^6$—C(═O)—R$^5$, —C(═O)—N(R$^5$)R$^6$ and —O—C(═O)—N(R$^5$)R$^6$; R$^5$ and R$^6$ are each independently a hydrogen atom or an alkyl group which has 1 to 10 carbon atoms and which may have a substituent; with the provision that if R$^5$ and/or R$^6$ is an alkyl group, the alkyl group may contain one selected from the group consisting of —O—, —S—, —O—C(═O)—, —C(═O)—O—, —O—C(═O)—O—, —NR$^7$—C(═O)—, —C(═O)—NR$^7$—, —NR$^7$— and —C(═O)—, except the case where two or more adjacent —O— and two or more adjacent —S— are contained in the alkyl group; and R$^7$ is a hydrogen atom or an alkyl group having 1 to 6 carbon atoms.

6. The left-handed-helix-inducing polymerizable chiral compound according to claim 1,
in the formula (I), wherein Y1 to Y6 each independently —C(═O)—O—, —O—C(═O)— or —O—;
wherein Yx and Yz are each —C(═O)—;
wherein G1 and G2 are each independently —(CH$_2$)$_6$— or —(CH$_2$)$_4$—;
wherein Z1 and Z2 are each independently CH$_2$═CH—;
wherein Q1 to Q4 are each independently a hydrogen atom or a methyl group;
wherein A1, A3, A4 and A6 are each independently a group represented by the following (A-i); and
wherein A2 and A5 are each independently a group represented by the following (A-i) or (A-ii):

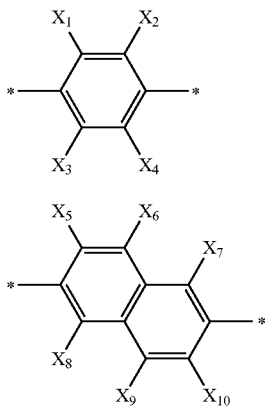

(A-i)

(A-ii)

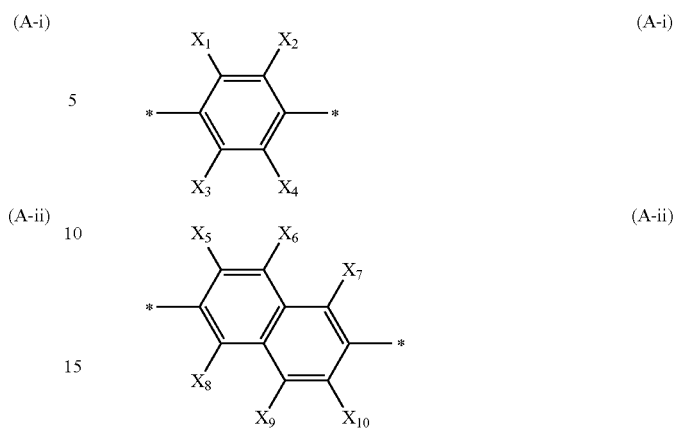

(A-i)

(A-ii)

wherein * represents a bond; $X_1$ to $X_{10}$ are each independently one selected from the group consisting of a hydrogen atom, a halogen atom, an alkyl group which has 1 to 10 carbon atoms and which may have a substituent, a cyano group, a nitro group, $-OR^5$, $-O-C(=O)-R^5$ and $-C(=O)-OR^5$; and $R^5$ is a hydrogen atom or an alkyl group which has 1 to 10 carbon atoms and which may have a substituent.

7. The left-handed-helix-inducing polymerizable chiral compound according to claim 1, in the formula (I), wherein a=b=0, and G1 and G2 are each —$CH_2CH_2C(=O)OCH_2CH_2$— or —$CH_2CH_2OC(=O)CH_2CH_2$—;

wherein A3 and A4 are each independently a group represented by the following (A-i); and wherein A2 and A5 are each independently a group represented by the following (A-i) or (A-ii):

wherein * represents a bond; $X_1$ to $X_{10}$ are each independently one selected from the group consisting of a hydrogen atom, a halogen atom, an alkyl group which has 1 to 10 carbon atoms and which may have a substituent, a cyano group, a nitro group, $-OR^5$, $-O-C(=O)-R^5$ and $-C(=O)-OR^5$; and $R^5$ is a hydrogen atom or an alkyl group which has 1 to 10 carbon atoms and which may have a substituent.

8. A left-handed helical, polymerizable liquid crystal composition comprising at least any one of the polymerizable chiral compounds defined by claim 1 and at least one kind of polymerizable liquid crystal compound.

9. A left-handed helical liquid crystal polymer obtained by polymerization of the left-handed helical, polymerizable liquid crystal composition defined by claim 8.

10. An optically anisotropic body comprising the left-handed helical liquid crystal polymer defined by claim 9 as a constitutional material.

* * * * *